United States Patent
Onomichi et al.

(10) Patent No.: US 9,329,193 B2
(45) Date of Patent: May 3, 2016

(54) SAMPLE PROCESSING APPARATUS AND SAMPLE PROCESSING METHOD

(75) Inventors: Hiromi Onomichi, Akashi (JP); Mitsuo Yamasaki, Kobe (JP)

(73) Assignee: SYSMEX CORPORATION, Hyogo (JP)

( * ) Notice: Subject to any disclaimer, the term of this patent is extended or adjusted under 35 U.S.C. 154(b) by 315 days.

(21) Appl. No.: 13/230,407

(22) Filed: Sep. 12, 2011

(65) Prior Publication Data
US 2012/0064638 A1    Mar. 15, 2012

(30) Foreign Application Priority Data
Sep. 10, 2010    (JP) .................................. 2010-203143

(51) Int. Cl.
*G01N 35/04*    (2006.01)
*G01N 35/10*    (2006.01)
*G01N 35/00*    (2006.01)

(52) U.S. Cl.
CPC .. *G01N 35/0092* (2013.01); *G01N 2035/00643* (2013.01); *G01N 2035/00891* (2013.01)

(58) Field of Classification Search
CPC ........................................... G01N 2035/00643
See application file for complete search history.

(56) References Cited

U.S. PATENT DOCUMENTS

| 2006/0024200 A1* | 2/2006 | Nishikiori et al. ............... 422/67 |
| 2006/0064270 A1* | 3/2006 | Onomichi et al. ............. 702/119 |
| 2009/0215183 A1* | 8/2009 | Takehara et al. ................ 436/47 |
| 2009/0263281 A1 | 10/2009 | Ushiku |

FOREIGN PATENT DOCUMENTS

| JP | 03-183955 A | 8/1991 |
| JP | U 3141576 | 4/2008 |

* cited by examiner

*Primary Examiner* — P. Kathryn Wright
(74) *Attorney, Agent, or Firm* — Sughrue Mion, PLLC

(57) ABSTRACT

A sample processing apparatus for performing a process including a plurality of steps on a sample, the sample processing apparatus sequentially processing a plurality of samples, is disclosed. The apparatus comprises a plurality of units corresponding to the respective steps in the process; a transfer section which transfers a sample to the units according to a flow of the steps; and a controller. Specifically, when an operation was not performed successfully, the controller interrupts the process for a sample that had not reached the location where the unsuccessful operation was performed while continuing the process for a sample that had already passed the location, retries the operation that was not performed successfully, and resumes the interrupted process when the retried operation has been performed successfully.

22 Claims, 15 Drawing Sheets

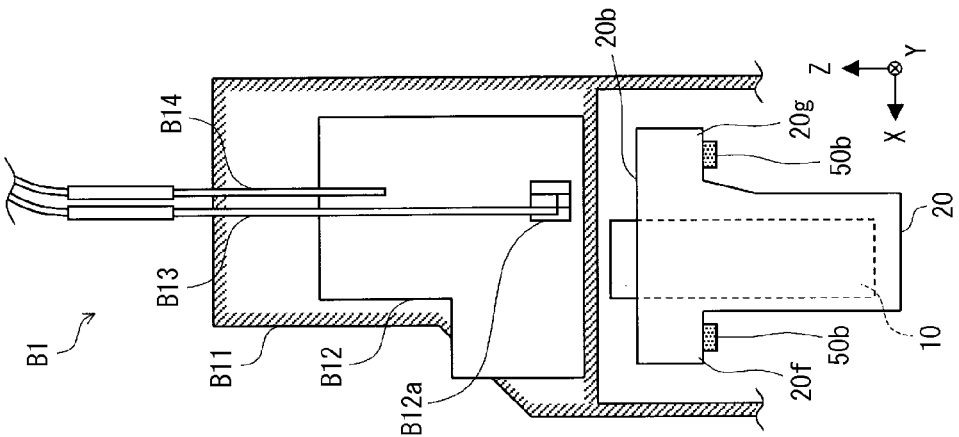

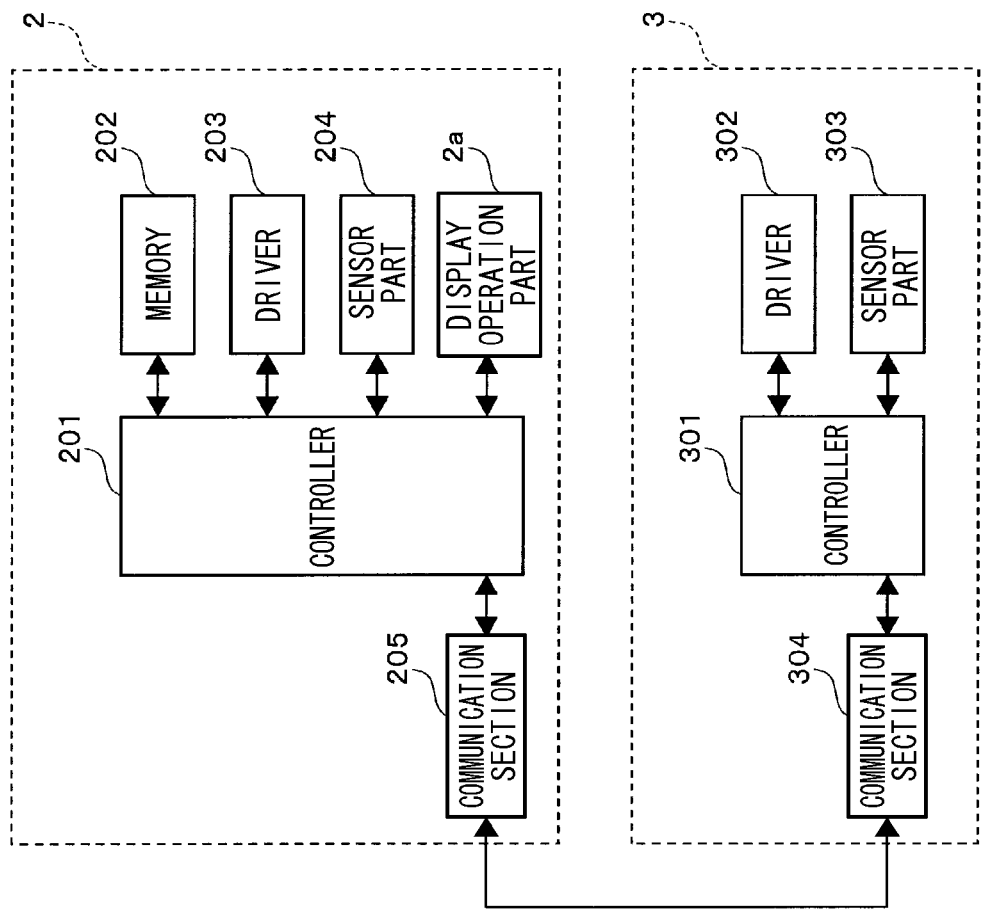
F I G. 5

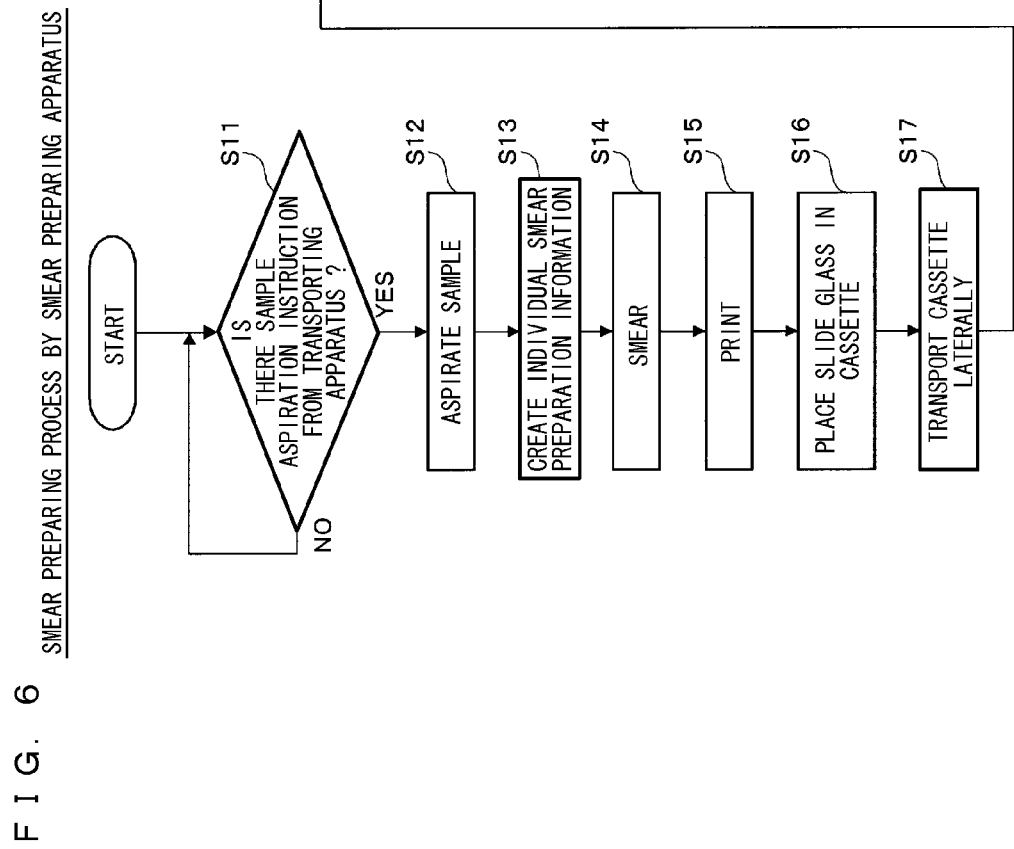
FIG. 6 SMEAR PREPARING PROCESS BY SMEAR PREPARING APPARATUS

F I G. 7A    INDIVIDUAL SMEAR PREPARATION INFORMATION

| ADMINISTRATION NUMBER | SAMPLE NUMBER | PREPARATION RESULT | STEP BEING PERFORMED |
|---|---|---|---|
| 1 | 1-1 | NORMAL | STEP 9 |
| 2 | 1-2 | NORMAL | STEP 8 |
| 3 | 1-3 | NORMAL | STEP 7 |
| 4 | 1-4 | NORMAL | STEP 6 |
| 5 | 1-5 | NORMAL | STEP 5 |
| ... | ... | ... | ... |

F I G. 7B    INDIVIDUAL SMEAR PREPARATION INFORMATION AT OCCURRENCE OF ERROR

| ADMINISTRATION NUMBER | SAMPLE NUMBER | PREPARATION RESULT | STEP BEING PERFORMED |
|---|---|---|---|
| 1 | 1-1 | NORMAL | STEP 40 |
| 2 | 1-2 | NORMAL | STEP 30 |
| 3 | 1-3 | LOW RELIABILITY | SUSPENSION FLAG ON IN STEP 25 |
| 4 | 1-4 | LOW RELIABILITY | SUSPENSION FLAG ON IN STEP 15 |
| 5 | 1-5 | LOW RELIABILITY | SUSPENSION FLAG ON IN STEP 10 |
| ... | ... | ... | ... |

NEW SAMPLE ASPIRATION RESUMPTION PROCESS

SAMPLE PROCESSING APPARATUS AND SAMPLE PROCESSING METHOD

FIELD OF THE INVENTION

The present invention relates to a sample processing apparatus and a sample processing method for aspirating a sample in a sample container and sequentially performing a plurality of processes onto the aspirated sample.

BACKGROUND

Conventionally, as a sample processing apparatus for aspirating a sample and sequentially performing a plurality of processes onto the sample, there are known sample processing apparatuses such as a smear preparing apparatus for aspirating a sample and preparing a smear on a slide glass, and a sample analyzer for aspirating a sample to be accommodated in a cuvette and analyzing the sample in the cuvette. It is also known that in such sample processing apparatuses, in a case where an abnormality occurs while a sample is being processed, processes of samples for which the processes can be continued are continued to be performed.

For example, in an automatic analyzer disclosed in Japanese Laid-open Patent Publication No. 3-183955, when it is determined that the abnormality is related to any one of specimen dispensers, reagent dispensers, and agitators, mechanism parts other than reaction tables and parts relating to optical measurements are stopped, thereby causing the automatic analyzer to be in a partially stopped state. Then, the automatic analyzer is controlled such that after optical measurement operations are finished with respect to a plurality of samples whose remaining processes have been optical measurement operations only, all parts of the automatic analyzer are stopped.

In such an automatic analyzer that is partially stopped in the case of an occurrence of an abnormality, if an abnormality occurs, processes of samples that have been temporally stopped due to the partial stop of the analyzer cannot be resumed until optical measurement operations are finished with respect to all of the samples whose remaining processes have been optical measurement operations only. Therefore, the automatic analyzer of Japanese Laid-open Patent Publication No. 3-183955 has a problem in that a suspension time of sample processing in the case of an occurrence of an abnormality is long.

SUMMARY OF THE PRESENT INVENTION

A first aspect of the present invention is a sample processing apparatus for performing a process including a plurality of steps on a sample, the sample processing apparatus sequentially processing a plurality of samples, the sample processing apparatus comprising: a plurality of units corresponding to the respective steps in the process, each unit performing a corresponding step; a transfer section which transfers a sample to the units according to a flow of the steps; and a controller which controls the transfer section and the units, wherein when an operation of the transfer section or one of the plurality of units was not performed successfully, the controller controls the transfer section and the plurality of units to: interrupt the process for a sample that had not reached the unit or the portion of the transfer section at which the operation was not performed successfully while continuing the process for a sample that had already passed the unit or a portion of the transfer section; retry the operation that was not performed successfully, and resume the interrupted process when the retried operation has been performed successfully.

A second aspect of the present invention is a sample processing method for processing a sample by performing a process comprising a plurality of steps, the method comprising: a transfer step of transferring a sample to a plurality of units according to a flow of the steps of the process, each of the units performing respective step in the process; a process step of sequentially performing the process on a plurality of samples such that the process on one sample and the process on other samples are partially overlapped; an interrupt step of interrupting, when a step in the process was not performed successfully, the process for a sample that had not been subjected to the unsuccessful step, while continuing the process for a sample that had already completed the unsuccessful step; a retry step for retrying the unsuccessful step; and a resumption step of resuming, when the retried step has been performed successfully, the interrupted process of the sample.

BRIEF DESCRIPTION OF THE DRAWINGS

FIG. 4A illustrates a state of an operation of a dispenser in which a base plate is fixed in a smear preparing apparatus according to embodiment 1;

FIG. 4B illustrates a state of an operation of the dispenser in which the tip portions of a discharge pipette and a supply pipette are located in an accommodating portion according to embodiment 1;

FIG. 4C illustrates a state of an operation of the dispenser in which the discharge pipette and the supply pipette are moved in an upward direction, and in which a stopper is moved in the upward direction according to embodiment 1;

FIG. 5 shows the outline of a configuration of the smear preparing apparatus and a transporting apparatus according to embodiment 1;

FIG. 6 is a flow chart showing a smear preparing process performed by the smear preparing apparatus according to embodiment 1;

FIG. 7A shows individual smear preparation information according to embodiment 1;

FIG. 7B shows the individual smear preparation information that is created in a case where a cassette arrival error or a cassette send-out error occurred according to embodiment 1;

DESCRIPTION OF THE PREFERRED EMBODIMENTS

Hereinafter, the present embodiments will be described with reference to the drawings.

Embodiment 1

The present embodiment is an embodiment in which the present invention is applied to a laboratory sample processing apparatus for preparing a smear of a blood sample. The laboratory sample processing apparatus according to the present embodiment includes a smear preparing apparatus and a transporting apparatus. Whether it is necessary to prepare a smear is determined, in general, based on results of analyses in previous stages on a blood sample performed by a blood analyzer and the like. In a case where a smear is prepared, a sample rack holding a sample container containing a blood sample is set on the transporting apparatus. Then, the sample rack is transported by the transporting apparatus and a smear is prepared by the smear preparing apparatus.

Hereinafter, the laboratory sample processing apparatus according to the present embodiment will be described with reference to the drawings.

Figure 1:
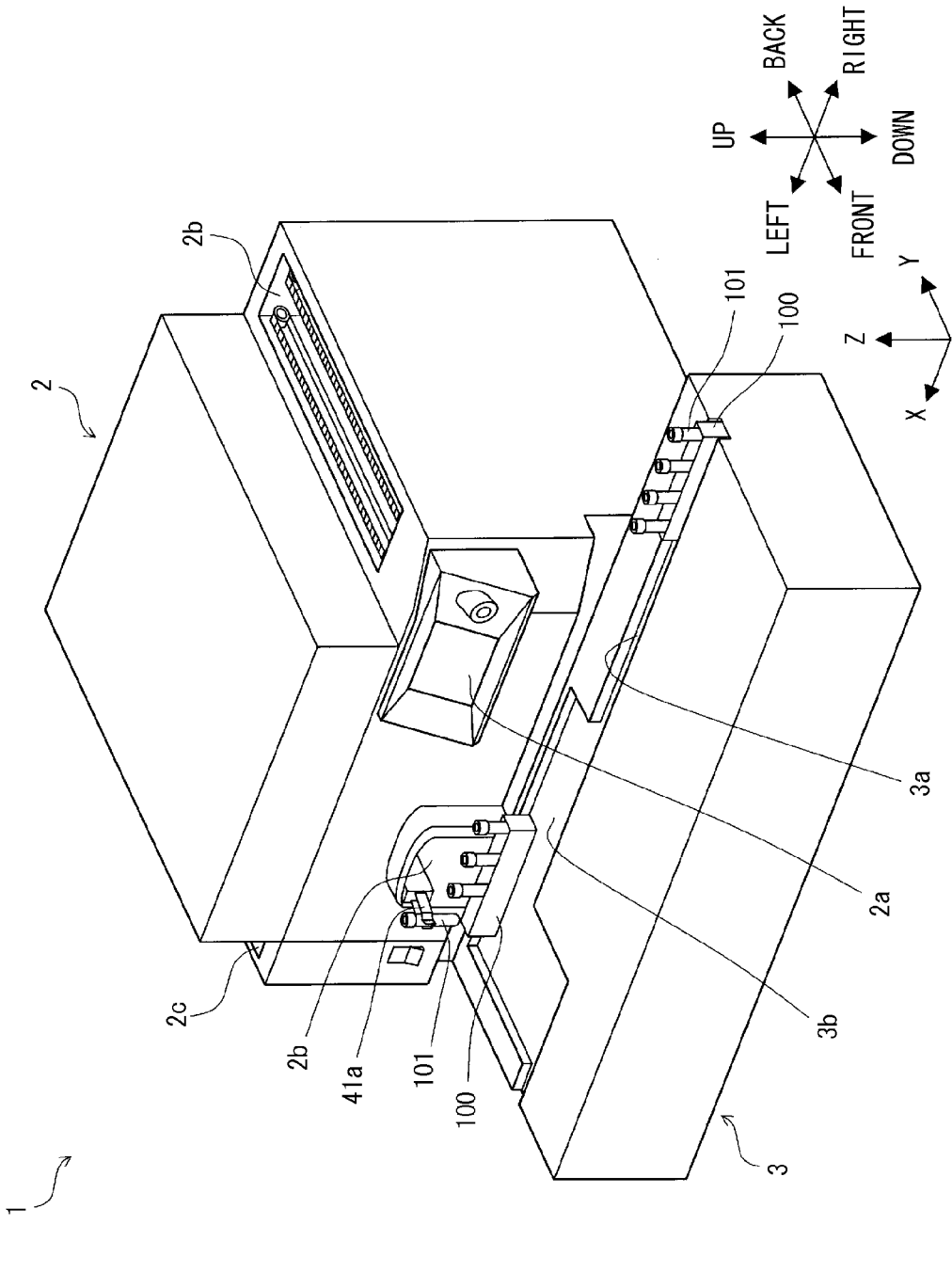
FIG. 1 is a perspective view showing a structure of a laboratory sample processing apparatus according to embodiment 1.

FIG. 1 is a perspective view showing the structure of a laboratory sample processing apparatus 1 according to the present embodiment. The laboratory sample processing apparatus 1 includes a smear preparing apparatus 2 and a transporting apparatus 3. Hereinafter, the X-axis positive direction will be referred to as the left direction; the X-axis negative direction will be referred to as the right direction, the Y-axis positive direction will be referred to as the backward direction, the Y-axis negative direction will be referred to as the forward direction, the Z-axis positive direction will be referred to as the upward direction, and the Z-axis negative direction will be referred to as the downward direction.

The smear preparing apparatus 2 includes a display operation part 2a composed of a touch panel provided on a front face of a cover thereof. Openings 2b, 2c, and 2d are provided on an upper right portion, an upper left portion, and on the front upper face of the cover of the smear preparing apparatus 2, respectively. The smear preparing apparatus 2 also includes a hand part 41a for holding a sample container 101 via the opening 2d. An user can control the smear preparing apparatus 2 by operating the display operation part 2a, set a cassette 20 in a below-described cassette accommodating part 47 (see FIG. 2) via the opening 2b, and take out the cassette 20 stored in a below-described cassette storage 51 (see FIG. 2) via the opening 2c.

The transporting apparatus 3 is provided at the front of the smear preparing apparatus 2, and includes a carry-in part 3a and a take-out part 3b. The transporting apparatus 3 transports a sample rack 100 located in the carry-in part 3a to the take-out part 3b. When the sample container 101 is located at the front of the hand part 41a, the sample container 101 is taken out by the hand part 41a to be drawn into the smear preparing apparatus 2.

Figure 2:
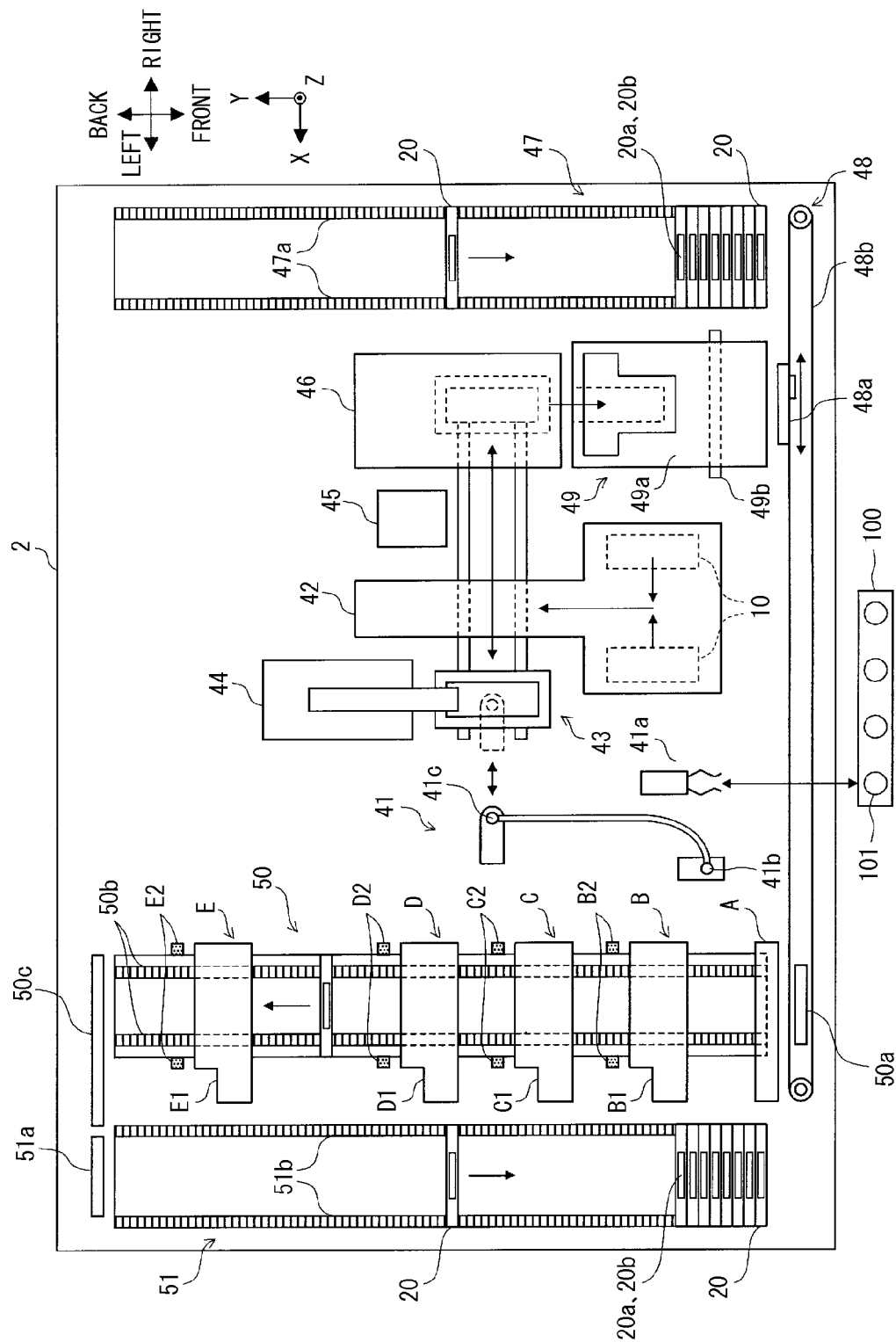
FIG. 2 is a plan view showing a structure of a smear preparing apparatus seen from above according to embodiment 1.

FIG. 2 is a plan view showing the structure of the smear preparing apparatus 2 seen from above.

The smear preparing apparatus 2 includes an aspirating/dispensing mechanism part 41, a slide glass feeder 42, a slide glass lateral feeder 43, a smearing mechanism part 44, a smear drying part 45, a printing part 46, the cassette accommodating part 47, a cassette lateral feeder 48, a cassette rotating part 49, a staining part 50, and the cassette storage 51.

The aspirating/dispensing mechanism part 41 includes the hand part 41a, a piercer (aspiration needle) 41b, and a dispensing pipette 41c. A sample container 101 located at the front of the hand part 41a is gripped by the hand part 41a, taken out of the sample rack 100, and agitated by the hand part 41a a predetermined number of times. Then, the blood sample contained in the sample container 101 is aspirated by the piercer 41b, and dropped by the dispensing pipette 41c movable in the left-right direction (X-axis directions), onto a slide glass 10 located at the front of the smearing mechanism part 44.

The slide glass feeder 42 holds a plurality of new slide glasses 10, and sequentially moves each of these new slide glasses 10 onto the slide glass lateral feeder 43. The slide glass lateral feeder 43 moves in the left direction (X-axis positive direction) each new slide glass 10 fed by the slide glass feeder 42, and locates it at the front of the smearing mechanism part 44.

When the blood sample is dropped on the slide glass 10 located at the front of the smearing mechanism part 44, the smearing mechanism part 44 smears the blood sample. The slide glass 10 including the smeared blood sample is moved in the right direction (X-axis negative direction) by the slide glass lateral feeder 43, and sequentially located at the front of the smear drying part 45 and then under the printing part 46. The smear drying part 45 dries the blood sample smeared on the slide glass 10 located at the front of the smear drying part 45 by means of a fan (not shown). The printing part 46 is composed of a printer (not shown), and prints the sample number, date, reception number, name, and the like on an edge portion of the slide glass 10.

The cassette accommodating part 47 includes a belt 47a that is movable in the forward direction (Y-axis negative direction). The user can set via the opening 2b (see FIG. 1) an empty cassette 20 on the belt 47a. The empty cassette 20 set on the belt 47a is transported in the forward direction by movement of the belt 47a.

Figure 3A:
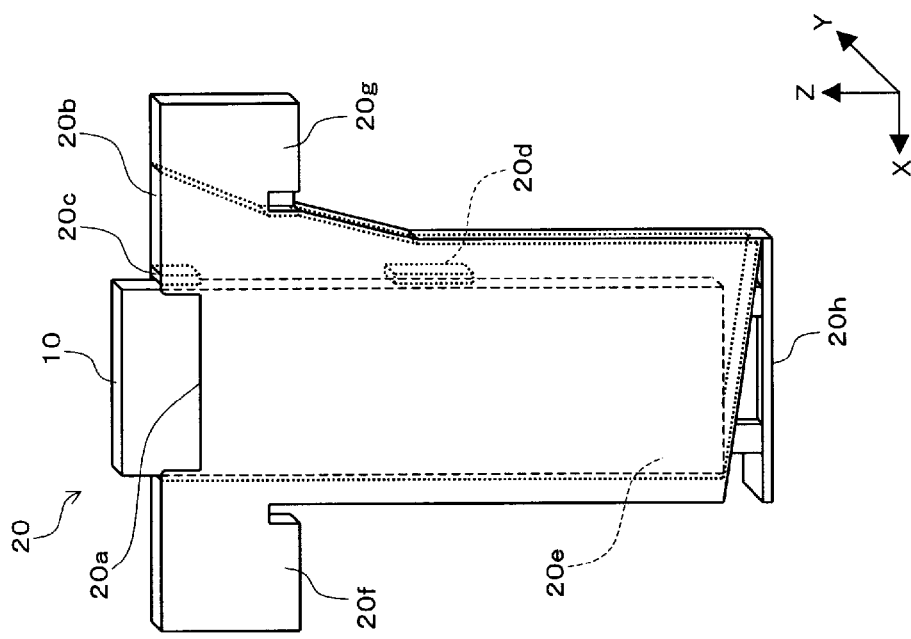
FIG. 3A is a perspective view showing a structure of a cassette according to embodiment 1.
Figure 3B:
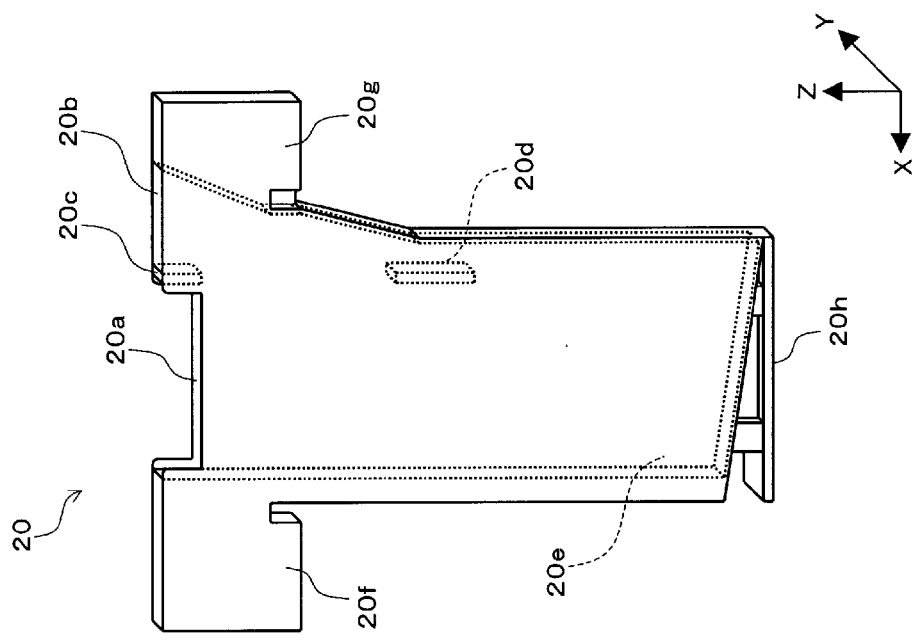
FIG. 3B is a perspective view showing a state where a slide glass is accommodated in a cassette according to embodiment 1.

Each of FIGS. 3A and 3B of is a perspective view showing the structure of the cassette 20. Each of FIGS. 3A and 3B also shows the coordinate axes used in FIG. 2, respectively, relative to the cassette 20 that is placed on the belt 47a.

With reference to FIG. 3A, the cassette 20 is composed of resin, and has a thickness in the Y-axis directions that allows a slide glass 10 to be accommodated in an accommodating portion 20e. In an upper portion of the cassette 20, accommodating openings 20a and 20b are formed side by side by being separated by a partition 20c. A partition 20d is provided downwardly from the partition 20c, and the accommodating portion 20e is formed inside the cassette 20. Shoulders 20f and 20g are formed on the left and right portions of the cassette 20, respectively, and the lower faces of the shoulders 20f and 20g are placed on the belt 47a by being supported from thereunder. A bottom 20h is formed in a lower part of the cassette 20. The slide glass 10 is inserted into the cassette 20 from above via the accommodating opening 20a.

FIG. 3B is a perspective view showing a state where the slide glass 10 is accommodated in the cassette 20. As shown in FIG. 3B, when the slide glass 10 is accommodated, a gap is created in an area, in the accommodating portion 20e, that is located to the right of the partitions 20c and 20d. This gap allows a pipette to be inserted via the accommodating opening 20b even when the slide glass 10 is accommodated in the cassette 20.

With reference back to FIG. 2, the cassette lateral feeder 48 includes a cassette supporting part 48a and a belt 48b that is movable in the left and right directions. The cassette supporting part 48a is fixed on the belt 48b, and is configured to support the bottom 20h of the cassette 20 in the upward direction. An empty cassette 20 located at the front of the cassette accommodating part 47 is supported by the cassette supporting part 48a and transported in the left direction, to be located at the front of the cassette rotating part 49.

The cassette rotating part 49 includes a plane 49a and a shaft 49b that is parallel to the X-axis direction. In accordance with rotation of the shaft 49b about the X-axis, the plane 49a becomes parallel to the X-Y plane or the X-Z plane. While the plane 49a is parallel to the X-Z plane, the empty cassette 20 located at the front of the cassette rotating part 49 is moved onto the plane 49a. Subsequently, the plane 49a is made parallel to the X-Y plane, and the slide glass 10 pushed out of the printing part 46 is inserted into the cassette 20 as shown in FIG. 2. Subsequently, the plane 49a is made parallel to the X-Z plane again, the cassette 20, which is accommodating the slide glass 10 and is on the plane 49a, is moved to the cassette supporting part 48a of the cassette lateral feeder 48. Then, the cassette 20 is transported in the left direction by the cassette lateral feeder 48 and located at the front of the staining part 50.

The staining part 50 includes a send-in mechanism part 50a, a belt 50b movable in the backward direction (Y-axis positive direction), stain mechanism parts A to E, and a send-out mechanism part 50c. The stain mechanism part B is composed of a dispenser B1 and a sensor B2, the stain mechanism part C is composed of a dispenser C1 and a sensor C2, the stain mechanism part D is composed of a dispenser D1 and a sensor D2, and the stain mechanism part E is composed of a dispenser E1 and a sensor E2.

In a state where the cassette 20 located at the front of the staining part 50 is supported by the cassette supporting part 48a of the cassette lateral feeder 48, the smear on the slide glass 10 accommodated in the cassette 20 is processed by the stain mechanism part A. Specifically, a pipette (not shown) of the stain mechanism part A is inserted via the accommodating opening 20b of the cassette 20, and the pipette ejects methanol into the accommodating portion 20e of the cassette 20. Then, the cassette 20 is sent onto the belt 50b by the send-in mechanism part 50a.

With respect to the cassette 20 sent onto the belt 50b by the send-in mechanism part 50a, the shoulders 20f and 20g are supported by the belt 50b. In this state, by movement of the belt 50b, the cassette 20 is transported in the backward direction. While the smear preparing apparatus 2 is operating, the belt 50b is always moving backward.

Each of the dispensers B1 to E1 processes the smear on the slide glass 10 accommodated in the cassette 20 located thereunder. Specifically, the dispenser B1 aspirates the methanol from the cassette 20 and ejects a stain solution 1 into the cassette 20. The dispenser C1 aspirates the stain solution 1 from the cassette 20 and ejects a diluent for the stain solution 1 into the cassette 20. The dispenser D1 aspirates the diluent for the stain solution 1 from the cassette 20 and ejects a diluent for a stain solution 2 into the cassette 20. The dispenser E1 aspirates the diluent for the stain solution 2 from the cassette 20 and cleans the inside of the cassette 20 with water. Operations performed by the dispenser B1 to E1 will be described later with reference to FIG. 4.

The sensors B2 to E2 are each a transmission-type sensor composed of a light emitter and a light receiver, and located slightly backward from the dispensers B1 to E1, respectively. The sensors B2 to E2 detect cassettes 20 that have been processed at the dispensers B1 to E1, moved backward, and then located between the light emitter and the light receiver of the sensors B2 to E2, respectively. Hereinafter, the position of a cassette 20 at which the cassette 20 is detected by each of the sensors B2 to E2 will be referred to as "passing position".

The cassette 20 transported to the back of the belt 50b is sent out in the left direction by the send-out mechanism part 50c. Accordingly, the cassette 20 is located behind the cassette storage 51.

The cassette storage 51 includes a send-in mechanism part 51a, and a belt 51b movable in the forward direction (Y-axis negative direction). The cassette 20 sent out by the send-out mechanism part 50c is sent onto the belt 51b by the send-in mechanism part 51a. The cassette 20 sent onto the belt 51b is transported in the forward direction by movement of the belt 51b. The cassette 20 located at a front part of the belt 51b is taken out via the opening 2c (see FIG. 1) by the user. Then, the smear preparation ends.

Next, with reference to FIG. 4, operations of the dispensers B1 to E1 will be described. Since the operation of the dispensers C1, D1, and E1 are substantially the same as the operation of the dispenser B1, only the operation of the dispenser B1 will be described for convenience.

FIGS. 4A to 4C are side views, respectively, when the dispenser B1 is seen in the Y-axis positive direction. The dispenser B1 includes a base plate B11, a stopper B12, a discharge pipette B13, and a supply pipette B14.

With reference to FIG. 4A, the base plate B11 is fixed in the smear preparing apparatus 2. The stopper B12 is a metal plate movable in the up-down direction (Z-axis directions) with respect to the base plate B11. A contact-type sensor B12a is set on the front face (a surface on the Y-axis negative direction side) of the stopper B12. The discharge pipette B13 and the supply pipette B14 are configured such that they can integrally move in the up-down direction. The discharge pipette B13 can aspirate a liquid in the cassette 20 and discharge the aspirated liquid, and the supply pipette B14 can eject a liquid into the cassette 20.

When the stopper B12 is located as shown in FIG. 4A, the rear face of the cassette 20 to be transported in the backward direction while being supported by the belt 50b abuts against the stopper B12 and stops. Hereinafter, the position of the cassette 20 at this time will be referred to as "stop position". At this time, the sensor B12a detects that the cassette 20 has been located at the stop position. In this state, the discharge pipette B13 and the supply pipette B14 are moved in the downward direction, and the tip portions of the discharge pipette B13 and the supply pipette B14 are located in the accommodating portion 20e of the cassette 20, as shown in FIG. 4B.

Subsequently, in the state shown in FIG. 4B, aspiration by the discharge pipette B13 and ejection by the supply pipette B14 are performed. After the aspiration and the ejection are finished, the discharge pipette B13 and the supply pipette B14 are moved in the upward direction, and further the stopper B12 is moved in the upward direction. This realizes the state shown in FIG. 4C, and the cassette 20 is moved in the backward direction while being supported by the belt 50b.

When the cassette 20 is moved slightly in the backward direction from the stop position of the dispenser B1 and is located at the passing position of the dispenser B1, the sensor B2 (see FIG. 2) detects the cassette 20. By this, it is known that the cassette 20 has passed the dispenser B1.

FIG. 5 shows the outline of the configuration of the smear preparing apparatus 2 and the transporting apparatus 3.

The smear preparing apparatus 2 includes a controller 201, a memory 202, a driver 203, a sensor part 204, the display operation part 2a, and a communication section 205.

The controller 201 controls each component of the smear preparing apparatus 2 by executing a computer program stored in the memory 202. The memory 202 is composed of a storage device such as a hard disk, and stores computer programs for causing the smear preparing apparatus 2 to operate. The memory 202 also stores information of steps regarding blood samples in the smear preparing apparatus 2 (hereinafter referred to as "individual smear preparation information"). Further, the memory 202 stores a setting regarding sample processing to be performed at the time when the smear preparing apparatus 2 is recovered from an abnormality (abnormality recovery setting). The abnormality recovery setting is a setting of, in a case of an occurrence of an abnormality, with respect to samples that are upstream of the site where the abnormality has occurred, whether to continue processes after the smear preparing apparatus 2 is recovered from the abnormality or to discard the samples. The individual smear preparation information and the abnormality recovery setting will be described later with reference to FIG. 7 and FIG. 9.

The driver 203 includes a mechanism for driving each component of the smear preparing apparatus 2, and is controlled by the controller 201. The sensor part 204 includes the contact-type sensors arranged on the front faces of the stoppers of the dispensers B1 to E1, the sensors B2 to E2, and in addition, other sensors within the smear preparing apparatus 2. Each sensor included in the sensor part 204 is controlled by the controller 201, and detection signals from the sensor part 204 are outputted to the controller 201.

The display operation part 2a is, as shown in FIG. 1, a touch panel having a display function and an input function integrally provided. When the display operation part 2a is operated by the user, a signal indicating the content of the operation is outputted to the controller 201. Further, the display operation part 2a is caused to display various types of information by the controller 201. The communication section 205 performs data communication with a communication section 304 of the transporting apparatus 3.

The transporting apparatus 3 includes a controller 301, a driver 302, a sensor part 303, and the communication section 304. The controller 301 controls each component of the transporting apparatus 3. The driver 302 includes a mechanism for driving each component of the transporting apparatus 3, and is controlled by the controller 301. The sensor part 303 includes sensors in the transporting apparatus 3, and is controlled by the controller 301. Detection signals from the sensor part 303 are outputted to the controller 301. The communication section 304 performs data communication with the communication section 205 of the smear preparing apparatus 2.

FIG. 6 is a flow chart showing a smear preparing process performed by the smear preparing apparatus 2. The smear preparing apparatus 2 of the present embodiment performs in parallel a smear preparing process composed of a plurality of steps shown in FIG. 6, on a plurality of samples. Here, the parallel performance of the process denotes that the process is performed on each of the plurality of samples with the start timing of the process shifted, such that while one step among steps S12 to S23 is being performed on one sample, another step among steps S12 to S23 is performed on another sample. The smear preparing apparatus 2 of the present embodiment continually aspirates a plurality of samples, and sequentially transfers the aspirated samples to units that are in charge of their corresponding steps among steps S12 to S23, and the units sequentially perform their process steps on the samples that have been transferred thereto, thereby realizing the parallel processing.

When the smear preparing process described below is performed, first, the transporting apparatus 3 locates a sample container 101 at the front of the hand part 41a (see FIGS. 1 and 2). At this time, a sample aspiration instruction is transmitted from the controller 301 of the transporting apparatus 3 to the controller 201 of the smear preparing apparatus 2.

Upon receiving the sample aspiration instruction from the transporting apparatus 3 (S11: YES), the controller 201 of the smear preparing apparatus 2 sequentially performs processes of S12 to S23. It should be noted that every time the controller 201 receives a sample aspiration instruction from the transporting apparatus 3, the controller 201 performs processes of S12 to S23 on a sample container 101 corresponding to the received instruction, in parallel with the processes of S12 to S23 that are being performed on other samples.

The controller 201 causes the piercer 41b to aspirate the blood sample from the sample container 101 gripped by the hand part 41a (S12). At this time, with respect to the blood sample, the controller 201 creates "individual smear preparation information" including information of a step being performed in the smear preparing apparatus 2 and the like, and stores the information in the memory 202 (S13).

FIG. 7A shows the individual smear preparation information.

The individual smear preparation information of each blood sample aspirated by the piercer 41b includes information of administration number, sample number, preparation result, step being performed, and the like, as shown in the rows in FIG. 7A. The administration number and the sample number are each uniquely assigned to a blood sample aspirated by the piercer 41b. Hereinafter, the blood sample identified by the administration number and the sample number is referred to as "identified sample".

The "preparation result" indicates whether the "step being performed" is being normally performed. The "step being performed" indicates in which step the identified sample is being processed in the smear preparing apparatus 2. It should be noted that the step number indicated in the column of the "step being performed" corresponds to a process performed in the smear preparing apparatus 2. For example, in the stain mechanism part B, a plurality of steps are performed such as a step of detecting arrival of the cassette 20, a step of detecting sending-out of the cassette 20, and a descending step, a discharge step and an ejection step regarding the discharge pipette B13 and the supply pipette B14. The controller 201 of the smear preparing apparatus 2 refers to the individual smear preparation information and determines at which step the identified sample is located.

With reference back to FIG. 6, the controller 201 causes the dispensing pipette 41c to drop the blood sample onto a slide glass 10 located at the front of the smearing mechanism part 44, and causes the smearing mechanism part 44 to smear the blood sample (S14).

Next, the controller 201 causes the slide glass 10 including the smear to move in the right direction, and causes the printing part 46 to print letters on the slide glass 10 (S15). Then, the controller 201 causes the cassette rotating part 49 to cause the slide glass 10 to be accommodated in a cassette 20 (S16). Subsequently, the controller 201 causes the cassette lateral feeder 48 to transport the cassette 20 to the front of the staining part 50 (S17).

Next, the controller 201 causes the stain mechanism parts A to E to sequentially perform processes of S18 to S22. That is, the stain mechanism part A dispenses methanol into the cassette 20 located at the front of the staining part 50 (S18). The stain mechanism part B aspirates the methanol from the cassette 20 located at the stop position of the stain mechanism part B, and ejects the stain solution 1 into the cassette 20 (S19). The stain mechanism part C aspirates the stain solution 1 from the cassette 20 located at the stop position of the stain mechanism part C, and ejects a diluent for the stain solution 1 into the cassette 20 (S20). The stain mechanism part D aspirates the diluent for the stain solution 1 from the cassette 20 located at the stop position of the stain mechanism part D, and ejects a diluent for the stain solution 2 into the cassette 20 (S21). The stain mechanism part E aspirates the diluent for the stain solution 2 from the cassette 20 located at the stop position of the stain mechanism part E, and cleans the inside of the accommodating portion 20e of the cassette 20 with water (S22).

Next, when the process performed by the stain mechanism part E ends, the controller 201 causes the send-out mechanism part 50c to send out the cassette 20 to the cassette storage 51 (S23). Then, the smear preparing process ends.

Figure 8:
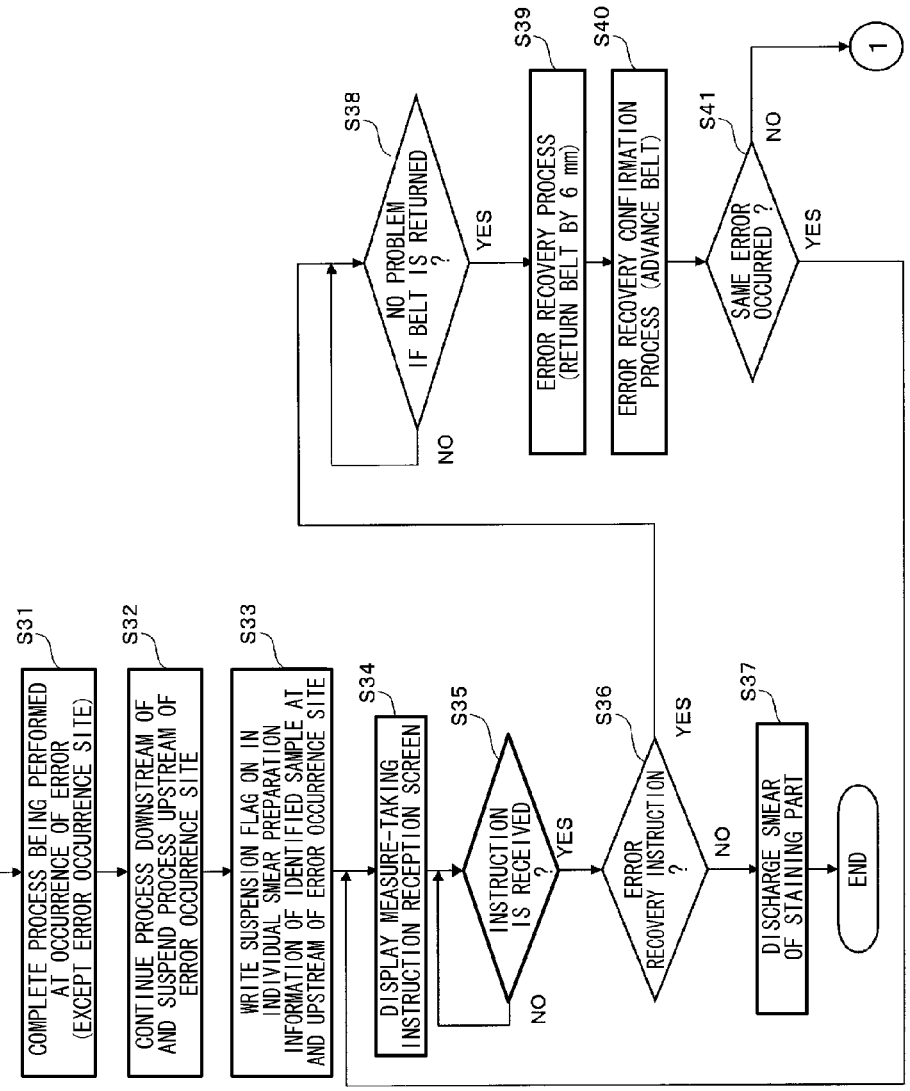
FIG. 8 is a flow chart showing processes performed by the smear preparing apparatus in a case where a cassette arrival error or a cassette send-out error occurred, according to embodiment 1.

FIG. 8 is a flow chart showing processes performed by the smear preparing apparatus 2 in a case where a cassette arrival error or a cassette send-out error occurred.

Here, the cassette arrival error denotes an error that occurs in a case where a cassette 20 that should arrive at the stop position of each of the stain mechanism parts B to E of the staining part 50 does not arrive at the stop position. For example, a cassette arrival error occurs in a case where a cassette 20 that has been sent onto the belt 50b by the send-in mechanism part 50a does not arrive at the stop position of the stain mechanism part B even after a predetermined period of time has elapsed from a timing at which the cassette 20 should have arrived there.

The cassette send-out error denotes an error that occurs in a case where a cassette 20 that should be detected at the passing position of each of the stain mechanisms part B to E of the staining part 50 is not detected. For example, a cassette send-out error occurs in a case where an cassette 20 at the stop position of the stain mechanism part B is moved in the backward direction by the belt 50b but does not arrive at the passing position at which the cassette 20 should be detected by the sensor B2 even after a predetermined period of time has elapsed after the timing at which the cassette 20 should have arrived at the passing position.

When either one of the errors has occurred in the smear preparing apparatus 2, the controller 201 of the smear preparing apparatus 2 causes the process at the site at which the error has occurred (error occurrence site), to be suspended. It should be noted that, at this time, the belt 50b is being normally moved in the backward direction.

Next, the controller 201 causes processes being performed (except the process being performed at the error occurrence site) in the smear preparing apparatus 2 at the time of the occurrence of the error, to be completed (S31). Then, the controller 201 causes processes downstream of the error occurrence site to be continued, and causes processes upstream of the error occurrence site to be suspended (S32).

Here, in a case where a cassette arrival error occurred due to an arrival failure of a cassette 20 that should have arrived at the stop position of a corresponding one of the stain mechanism parts B to E, the error occurrence site is the corresponding one of the stain mechanism parts B to E. In a case where a cassette send-out error occurred due to an arrival failure of a cassette 20 that should have arrived at the passing position of a corresponding one of the stain mechanism parts B to E, the error occurrence site is the corresponding one of the stain mechanism parts B to E. At the respective error occurrence sites of the stain mechanism parts B to E, the processes S12 to S19, the processes S12 to S20, the processes S12 to S21, and the processes S12 to S22 in FIG. 6 are suspended, respectively.

Next, the controller 201 writes "suspension flag ON" in the individual smear preparation information of each of the identified samples that are located at the error occurrence site and upstream of the error occurrence site (S33).

FIG. 7B shows the individual smear preparation information that is created in a case where a cassette arrival error or a cassette send-out error occurred.

In FIG. 7B, it is assumed that the administration numbers of the identified samples downstream of the error occurrence site are 1 and 2, and that the administration numbers of the identified samples at and upstream of the error occurrence site are 3 or greater. At this time, when the process of S33 in FIG. 8 is performed, in the item "step being performed" of each identified sample whose administration number is 3 or greater, the step at which the identified sample is located and "suspension flag ON" are written as shown in FIG. 7B.

With reference back to FIG. 8, next, the controller 201 of the smear preparing apparatus 2 causes the display operation part 2a to display a measure-taking instruction reception screen (S34).

Figure 10B:
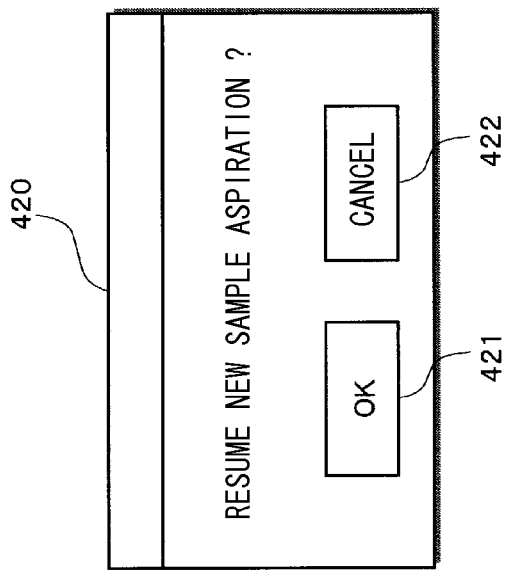
FIG. 10B shows a configuration of a sample aspiration instruction reception screen displayed on the display operation part.
Figure 10A:
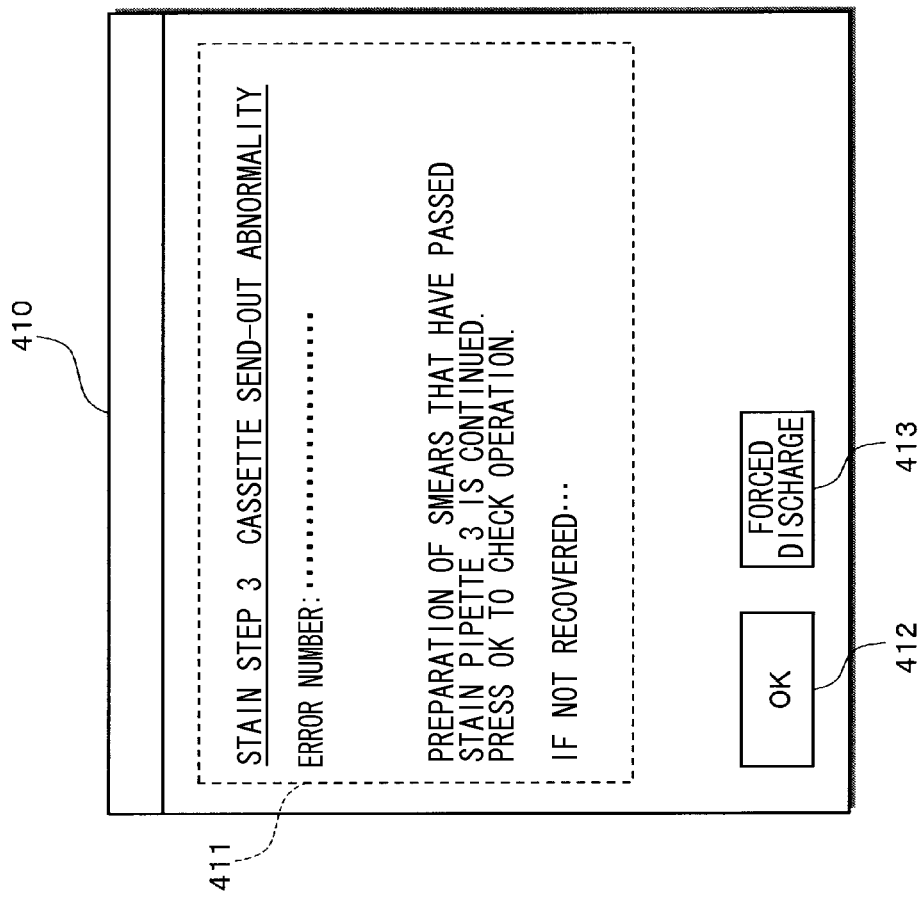
FIG. 10A shows a configuration of a measure-taking instruction reception screen displayed on a display operation part according to embodiment 1 and a configuration of a sample aspiration instruction reception screen displayed on the display operation part.

FIG. 10A shows the configuration of a measure-taking instruction reception screen 410 displayed on the display operation part 2a in S34 in FIG. 8.

The measure-taking instruction reception screen 410 includes a message display part 411, an OK button 412, an example of a first instruction part, and a forced discharge button 413, an example of a second instruction part. In the message display part 411, the step at which the error occurred, the detail of the error, the error number, measures to be taken, and the like are displayed. In FIG. 10A, it is indicated that a cassette send-out error occurred in the stain mechanism part D. The user can press the OK button 412 or the forced discharge button 413.

With reference back to FIG. 8, when the controller 201 of the smear preparing apparatus 2 receives an instruction by the OK button 412 or the forced discharge button 413 being pressed (S35: YES), the process is advanced to S36.

When the content of the instruction received at S35 is not an error recovery instruction (S36: NO), that is, when the forced discharge button 413 was pressed, the controller 201 causes all the smears in the staining part 50 to be discharged (S37). In this case, smears and cassettes 20 located upstream of the staining part 50 are not discharged, and held at the respective positions when they were caused to be suspended.

On the other hand, when the content of the instruction received at S35 is an error recovery instruction (S36: YES), that is, the OK button 412 was pressed, the controller 201 determines whether there is no problem if the belt 50*b* is retuned in the forward direction (Y-axis negative direction) (S38). That is, at this time, it is determined whether returning the belt 50*b* in the forward direction causes any problem in processes that are being continued on the downstream side of the error occurrence site. For example, in a case where an error has occurred in the stain mechanism part B, if a pipette is being inserted in a cassette 20 located at the stop position of the stain mechanism part D where the process is being continued, returning the belt 50*b* in the forward direction will cause a problem in the dispensing and ejecting process. The controller 201 determines whether such a problem occurs.

Upon determining that there is no problem if the belt 50*b* is returned in the forward direction (S38: YES), the controller 201 performs an error recovery process (S39). Specifically, the controller 201 moves the belt 50*b* by 6 mm in the forward direction. Subsequently, the controller 201 performs an error recovery confirmation process (S40). Specifically, the controller 201 moves the belt 50*b* in the backward direction as in the normal operation.

In a case where the same error has occurred irrespective of the performance of the error recovery confirmation process (S41: YES), the process is returned to S34. On the other hand, in a case where the same error does not occur as a result of the error recovery confirmation process (S41: NO), the process is advanced to terminal 1.

Figures 9A, 9B:
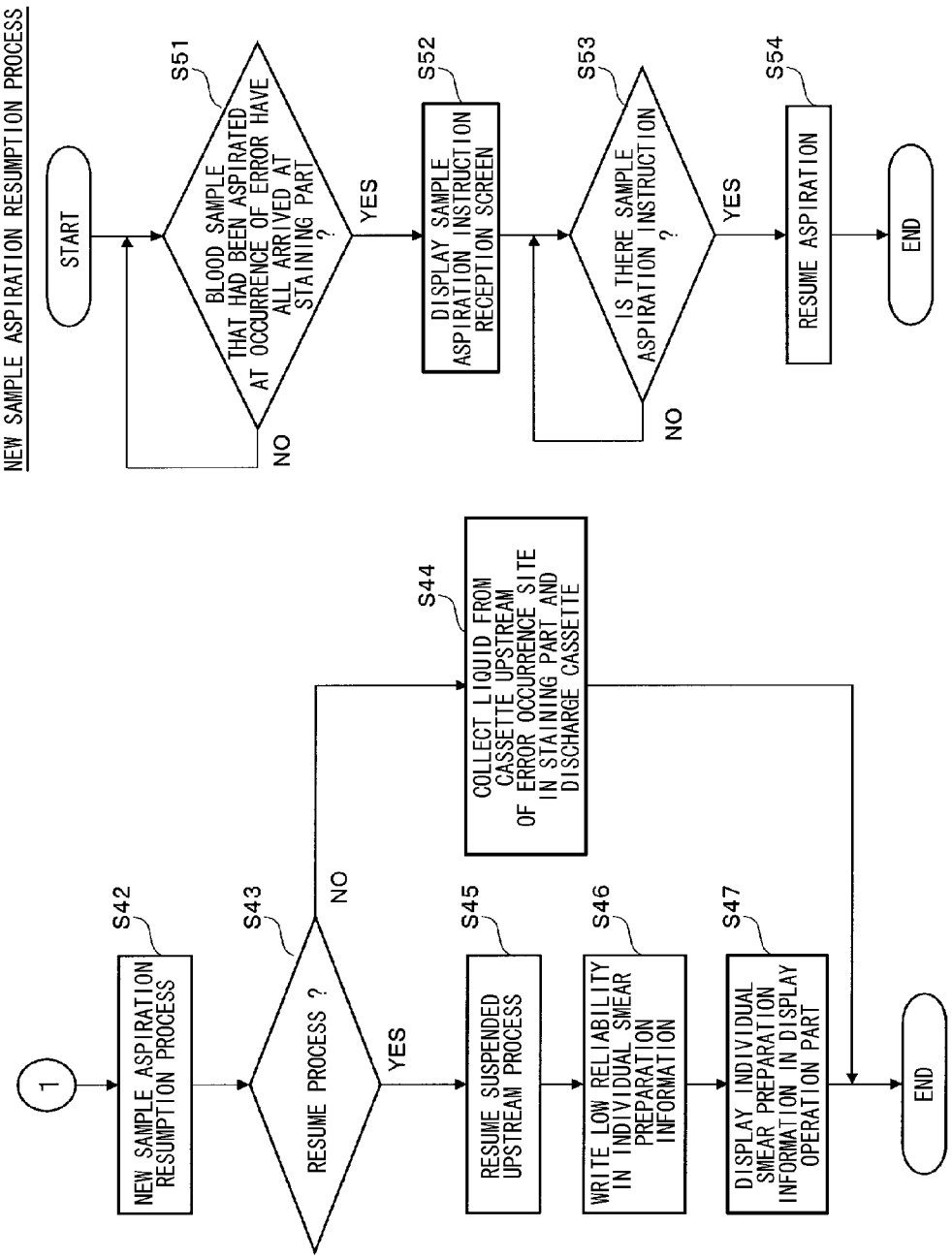
FIG. 9A is a flow chart showing processes performed by the smear preparing apparatus in a case where a cassette arrival error or a cassette send-out error occurred and a flow chart showing a new sample aspiration resumption process, according to embodiment 1.
FIG. 9B is a flow chart showing the new sample aspiration resumption process according to embodiment 1.

FIG. 9A is a flow chart showing processes after terminal 1 in FIG. 8.

The controller 201 of the smear preparing apparatus 2 performs a new sample aspiration resumption process (S42). The new sample aspiration resumption process will be described later with reference to FIG. 9B.

Next, when an abnormality recovery has been performed, the controller 201 refers to the abnormality recovery setting and determines whether to resume the suspended processes on corresponding samples (S43). It should be noted that the abnormality recovery setting is set by the user in advance via the display operation part 2*a* of the smear preparing apparatus 2. The abnormality recovery setting is stored in the memory 202.

In a case where the abnormality recovery setting is set to "do not resume process" (S43: NO), the controller 201 causes the liquid in cassettes 20 that are located upstream of the error occurrence site in the staining part 50 to be collected, and at the same time, causes the cassettes 20 to be discharged into the cassette storage 51 (S44). In this case, smears and cassettes 20 that are located on the upstream side of the staining part 50 are not discharged, and held at the respective positions where they were caused to be suspended.

On the other hand, in a case where the abnormality recovery setting is set to "resume process" (S43: YES), the controller 201 resumes all of the suspended processes on the upstream side of the error occurrence site (S45). It should be noted that aspiration of a new sample by the piercer 41*b* is not resumed by the process of S45. Aspiration of a new sample is resumed by a below-described new sample aspiration resumption process.

Next, the controller 201 writes, in the individual smear preparation information of each of the identified samples that are located upstream of the error occurrence site in the staining part 50, that the sample is a low reliability smear (S46). For example, as shown in FIG. 7B, "low reliability" is written in the item "preparation result" of a corresponding administration number.

Next, the controller 201 causes the display operation part 2*a* to display the individual smear preparation information of identified samples that have been classified as low reliability smears (S46). The individual smear preparation information indicated in a table format as shown in FIG. 7B is shown in the display operation part 2*a*. Then, the processes performed by the smear preparing apparatus 2 at the occurrence of error end.

FIG. 9B is a flow chart showing the new sample aspiration resumption process performed in S42. At the time when this process is started, aspiration by the piercer 41*b* is being suspended, as described in the process of S32 in FIG. 8.

The controller 201 of the smear preparing apparatus 2 determines whether all of the blood samples that had already been aspirated at the time of the occurrence of a cassette arrival error or a cassette send-out error have arrived at the staining part 50 (whether the processes of S14 to S17 in FIG. 6 have ended) (S51). The controller 201 performs this determination with reference to the "step being performed" indicated in the individual smear preparation information. When all of such blood samples have arrived at the staining part 50 (S51: YES), the controller 201 causes the display operation part 2*a* to display a sample aspiration instruction reception screen (S52).

FIG. 10B shows the configuration of a sample aspiration instruction reception screen 420 displayed on the display operation part 2*a*. The sample aspiration instruction reception screen 420 includes an OK button 421 and a cancel button 422. The user can press the OK button 421 or the cancel button 422.

With reference back to FIG. 9B, upon determining that the OK button 421 on the sample aspiration instruction reception screen 420 has been pressed (S53: YES), the controller 201 of the smear preparing apparatus 2 causes the smear preparing apparatus 2 to resume aspiration (S54). Accordingly, each sample container 101 located at the front of the hand part 41*a* is sequentially gripped by the hand part 41*a*, and the piercer 41*b* aspirates the sample. Then, the new sample aspiration resumption process ends.

As described above, according to the present embodiment, in a case where a cassette arrival error or a cassette send-out error occurred in any of the stain mechanism parts B to E, processes upstream of the error occurrence site are suspended, and then an error recovery process to return the belt by 6 mm is performed. Accordingly, relatively minor errors such as a cassette 20 being caught by the belt 50*b* or cassettes 20 being stuck to each other can be solved.

Moreover, in such a case, processes downstream of the error occurrence site are continued. Accordingly, processes of the smears that have passed the error occurrence site can be promptly completed.

Further, according to the present embodiment, by setting the abnormality recovery setting to "resume process", the suspended processes are resumed after the error is solved. Accordingly, there is no need to discard the smears for which processes have been suspended, and thus, there is no need to perform processes such as staining smears again, whereby the discard amount of the consumables can be reduced. Such a reduction of the discard amount of consumables is also effective in term of environmental conservation.

Further, in this case, with respect to the blood samples and smears (identified samples) for which processes were suspended, "low reliability" is written in the preparation result column of their individual smear preparation information. Moreover, the individual smear preparation information of the identified samples for which processes were suspended is displayed in the display operation part 2*a*. Accordingly, the user can distinguish identified samples for which processes ended without having been suspended, from identified samples for which processes were suspended.

Embodiment 2

The present embodiment is an embodiment in which the present invention is applied to an immune analyzer for performing tests for various items such as hepatitis B, hepatitis C, tumor marker, and thyroid hormone, by using samples such as blood.

Hereinafter, an immune analyzer according to the present embodiment will be described with reference to the drawings.

Figure 11:
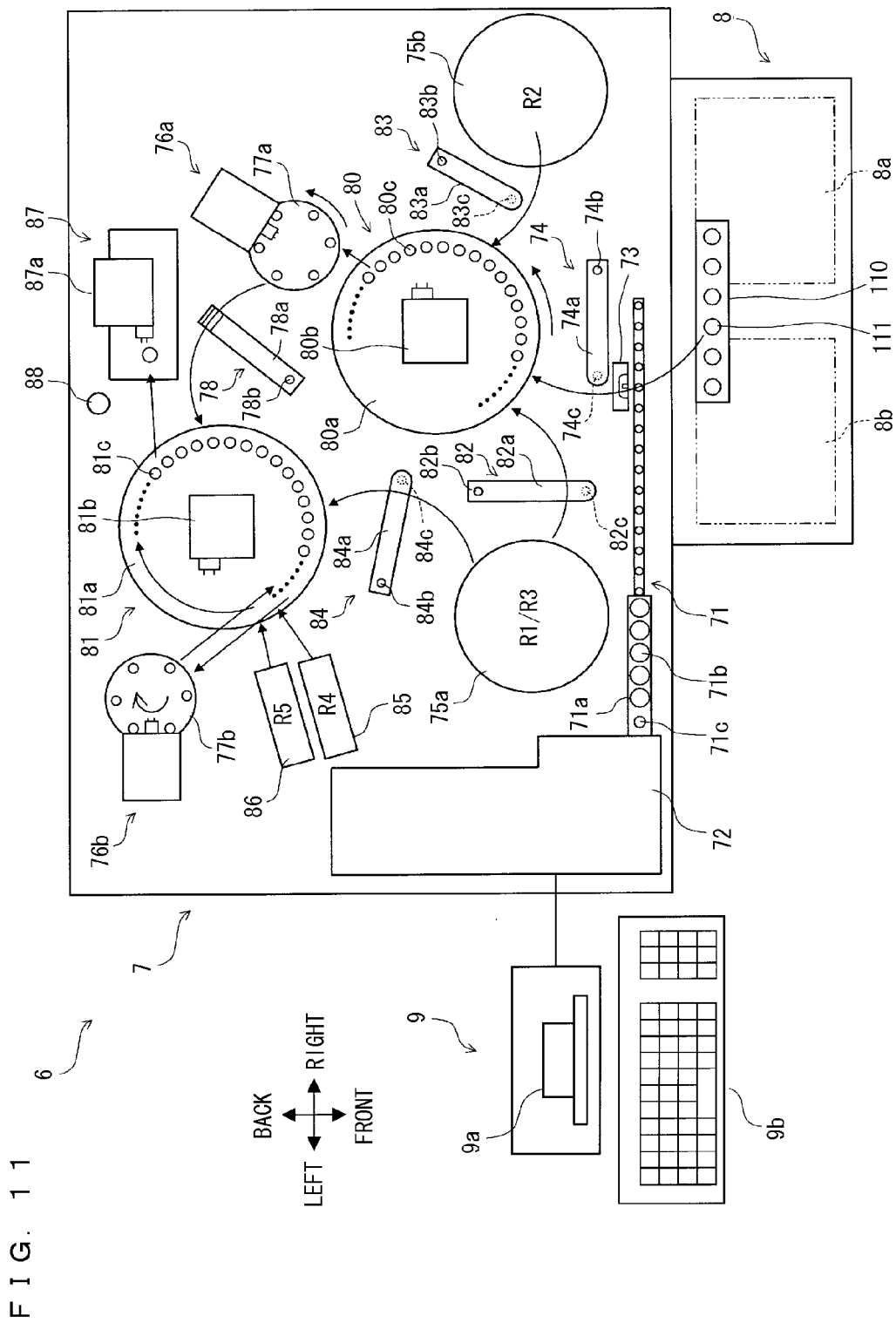
FIG. 11 is a plan view showing a structure of an immune analyzer seen from above according to embodiment 2.

FIG. 11 is a plan view showing the structure of an immune analyzer 6 seen from above according to the present embodiment. The immune analyzer 6 includes a measurement unit 7, a sample transporting unit 8 provided at the front of the measurement unit 7, and a control apparatus 9 electrically connected to the measurement unit 7.

The measurement unit 7 includes an urgent sample/tip transporter 71, a pipette tip supplying apparatus 72, a tip detachment part 73, a sample dispenser 74, reagent tables 75a and 75b, a primary B/F (Bound Free) separator 76a, a secondary B/F separator 76b, a primary B/F separation table 77a, a secondary B/F separation table 77b, a primary reaction part 80, a secondary reaction part 81, reagent dispensers 82 to 84, an R4 reagent dispenser 85, an R5 reagent dispenser 86, a detector 87, and a discard hole 88. In the immune analyzer 6 according to the present embodiment, in order to prevent a sample such as blood aspirated and ejected by the sample dispenser 74 from being mixed with other samples, each time a sample is aspirated and ejected, a disposable pipette tip is replaced with a new one.

In the immune analyzer 6, a sample to be measured such as blood and a buffer (R1 reagent) are mixed together, and to this resultant mixed solution, added is a reagent (R2 reagent) containing magnetic particles carrying a capture antibody that is to be bound to an antigen contained in the sample. The magnetic particles carrying the capture antibody bound to the antigen are attracted to a magnet of the primary B/F separator 76a, whereby the components contained in the sample that were not bound to the capture antibody are removed. Then, a labeled antibody (R3 reagent) is further added, and the magnetic particles carrying the capture antibody bound to the antigen and the labeled antibody are attracted by a magnet of the secondary B/F separator 76b, whereby the R3 reagent containing unreacted labeled antibody is removed. Further, a dispersion liquid (R4 reagent) and a luminescent substrate (R5 reagent) that emits light in the course of a reaction with the labeled antibody are added. Thereafter, the amount of light generated by the reaction of the luminescent substrate with the labeled antibody is measured. Through these procedures, the antigen contained in the sample and bound to the labeled antibody is quantitatively measured.

The sample transporting unit 8 includes a rack setting part 8a in which racks 110 each accommodating test tubes 111 each containing an unprocessed sample are set, and a rack storing part 8b for storing racks 110 each accommodating test tubes 111 each containing a sample for which a dispensing process has been performed. The sample transporting unit 8 transports a rack 110 accommodating a plurality of test tubes 111 each containing a sample, to a position corresponding to the aspirating position of the sample dispenser 74. When a test tube 111 containing an unprocessed sample is transported to the position corresponding to the aspirating position of the sample dispenser 74, the sample dispenser 74 aspirates the sample such as blood contained in the test tube 111. Then, the rack 110 accommodating the test tube 111 is stored in the rack storing part 8b.

The urgent sample/tip transporter 71 includes a transporting rack 71a in which test tube setting parts 71b and a tip setting part 71c are formed. Each test tube setting part 71b is configured to hold a test tube 111 containing an urgent sample that needs to take precedence in front of samples transported by the sample transporting unit 8, and that needs an urgent test to be performed. The test tube 111 held in the test tube setting part 71b is transported to the position corresponding to the aspirating position of the sample dispenser 74.

The pipette tip supplying apparatus 72 has a function of placing pipette tips that have been provided, one by one, in the tip setting part 71c of the transporting rack 71a of the urgent sample/tip transporter 71. The tip detachment part 73 is provided so as to detach the pipette tip attached to the sample dispenser 74 described below.

The sample dispenser 74 includes an arm 74a, a shaft 74b, and a pipette 74c. The arm 74a is rotatable about the shaft 74b and movable in the up-down direction. The pipette 74c is provided at a tip portion of the arm 74a, and aspirates and ejects a sample. A pipette tip transported by the tip setting part 71c of the urgent sample/tip transporter 71 is attached to the tip of the pipette 74c. The sample dispenser 74 dispenses the sample in the test tube 111 transported by the sample transporting unit 8 into a cuvette (not shown) held in a holder 80c in a primary reaction table 80a of the primary reaction part 80 described below.

The reagent table 75a is a turntable which is rotationally driven. Reagent containers each containing the buffer (R1 reagent) and reagent containers each containing the R3 reagent containing the labeled antibody are set on the reagent table 75a. The reagent table 75b is a turntable which is rotationally driven. Reagent containers each containing the R2 reagent containing the magnetic particles carrying the capture antibody are set on the reagent table 75b.

The primary reaction part 80 includes the primary reaction table 80a and a container transporter 80b. Holders 80c each for holding a cuvette are formed in the primary reaction table 80a. The primary reaction table 80a transports cuvettes each containing a sample, the R1 reagent, and the R2 reagent in the rotation direction. The container transporter 80b transports each cuvette to the primary B/F separation table 77a described below.

Here, the primary reaction part 80 is provided so as to transfer by rotation the cuvettes held in the holders 80c in the rotationally-driven primary reaction table 80a by a predetermined angle every predetermined period of time (20 seconds in the present embodiment), and to agitate the sample, the R1 reagent, and the R2 reagent in the cuvettes. That is, the primary reaction part 80 is provided to cause the R2 reagent containing the magnetic particles to react with the antigen in the sample in each cuvette.

The reagent dispenser 82 includes an arm 82a, a shaft 82b, and a pipette 82c. The arm 82a can pivot about the shaft 82b and move in the up-down direction. The pipette 82c is provided at a tip portion of the arm 82a, and aspirates the R1 reagent in a reagent container and ejects the aspirated R1 reagent. The reagent dispenser 82 aspirates the R1 reagent in a reagent container set on the reagent table 75a and dispenses the aspirated R1 reagent into a cuvette in the primary reaction part 80.

A reagent dispenser 83 includes an arm 83a, a shaft 83b, and a pipette 83c. The arm 83a can pivot about the shaft 83b and move in the up-down direction. The pipette 83c is provided at a tip portion of the arm 83a, and aspirates the R2 reagent in a reagent container and ejects the aspirated R2 reagent. The reagent dispenser 83 dispenses the R2 reagent in a reagent container set on the reagent table 75*b*, into a cuvette that is held in the primary reaction part 80 and in which the sample and the R1 reagent has been dispensed.

The primary B/F separator 76*a* is provided so as to separate the magnetic particles carrying the capture antibody bound to the antigen contained in the sample from unreacted components which were not bound to the capture antibody, in the specimen in a cuvette transported by the container transporter 80*b* of the primary reaction part 80. The cuvette that is on the primary B/F separation table 77*a* and from which the unreacted components have been removed is transported by a transport mechanism 78 to a holder 81*c* in a secondary reaction table 81*a* of the secondary reaction part 81.

The transport mechanism 78 is configured to be able to cause an arm 78*a* having a cuvette grip portion (not shown) at the tip thereof to pivot about the shaft 78*b*, and to move the arm 78*a* in the up-down direction.

The secondary reaction part 81 has a similar configuration to that of the primary reaction part 80, and includes the secondary reaction table 81*a* and a container transporter 81*b*. Holders 81*c* each for holding a cuvette are formed in the secondary reaction table 81*a*. The secondary reaction table 81*a* transports cuvettes each containing a sample, the R1 reagent, the R2 reagent, the R3 reagent, the R4 reagent, and the R5 reagent in the rotation direction. The container transporter 81*b* transports each cuvette to the secondary B/F separation table 77*b* described below, and transports the cuvette processed by the secondary B/F separator 76*b* to a holder 81*c* in the secondary reaction table 81*a* again.

Here, the secondary reaction part 81 is provided so as to transfer by rotation the cuvettes held in the holders 81*c* in the rotationally-driven secondary reaction table 81*a* by a predetermined angle every predetermined period of time (20 seconds in the present embodiment), and to agitate the sample, the R1 reagent, the R2 reagent, the R3 reagent, the R4 reagent, and the R5 reagent in the cuvettes. That is, the secondary reaction part 81 is provided to cause the R3 reagent containing the labeled antibody to react with the antigen in the sample and to cause the R5 reagent containing the luminescent substrate to react with the labeled antibody in the R3 reagent, in each cuvette.

The reagent dispenser 84 includes an arm 84*a*, a shaft 84*b*, and a pipette 84*c*. The arm 84*a* can pivot about the shaft 84*b* and move in the up-down direction. The pipette 84*c* is provided at a tip portion of the arm 84*a*, and aspirates the R3 reagent in a reagent container and ejects the aspirated R3 reagent. The reagent dispenser 84 aspirates the R3 reagent in a reagent container set on the reagent table 75*a* and dispenses the aspirated R3 reagent into a cuvette that is held in the secondary reaction part 81 and in which the sample, the R1 reagent, and the R2 reagent have been dispensed.

The secondary B/F separator 76*b* has a similar configuration to that of the primary B/F separator 76*a*, and is provided so as to separate the labeled antibody bound to the magnetic particles via the capture antibody and the antigen, from unreacted labeled antibody, in the specimen in a cuvette transported by the container transporter 81*b* of the secondary reaction part 81.

The R4 reagent dispenser 85 and the R5 reagent dispenser 86 are provided so as to supply the R4 reagent and the R5 reagent, respectively, to a cuvette in the secondary reaction part 81, by moving respective nozzle portions thereof (not shown) in the up-down direction.

The detector 87 includes a transport mechanism part 87*a* for transporting to the detector 87 a cuvette held in a holder 81*c* in the secondary reaction table 81*a* of the secondary reaction part 81. The detector 87 obtains, by means of a photo multiplier tube, the amount of light generated in the course of the reaction between the luminescent substrate and the labeled antibody bound to the antigen in the sample on which predetermined processes have been performed, thereby measuring the amount of the antigen contained in the sample.

The discard hole 88 is provided so as to discard cuvettes containing specimens that have been measured. Each cuvette containing a measured specimen is transported by the transport mechanism part 87*a* of the detector 87 to a position below an aspirator (not shown). The measured specimen is aspirated by the aspirator and the cuvette is emptied. Then, the cuvette is transported by the transport mechanism part 87*a* to a position corresponding to the discard hole 88, and then discarded, through the discard hole 88, into a dust box (not shown) that is provided below the immune analyzer 6.

The control apparatus 9 is composed of a personal computer or the like, and includes a display unit 9*a* and an input unit 9*b*. The control apparatus 9 controls operations of mechanisms in the measurement unit 7, and analyzes optical information of the sample obtained in the measurement unit 7. The user can confirm information such as an analysis result of the sample via the display unit 9*a*, and can perform control and the like of the measurement unit 7 via the input unit 9*b*.

Figure 12:
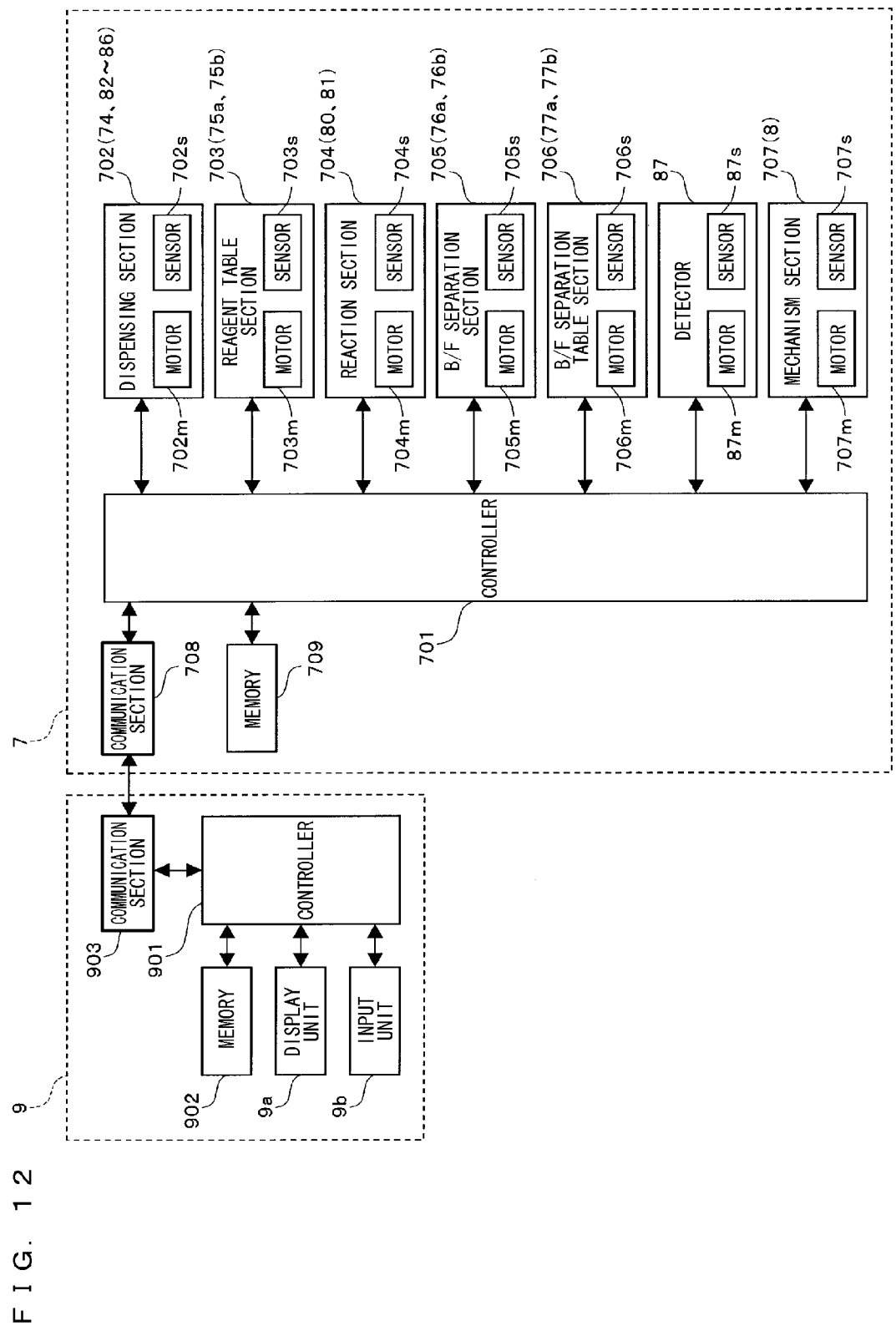
FIG. 12 shows the outline of a configuration of a measurement unit and a control apparatus according to embodiment 2.

FIG. 12 shows the outline of the configuration of the measurement unit 7 and the control apparatus 9.

The measurement unit 7 includes a controller 701, a dispensing section 702, a reagent table section 703, a reaction section 704, a B/F separation section 705, a B/F separation table section 706, the detector 87, a mechanism section 707, a communication section 708, and a memory 709.

The controller 701 executes a control program stored in the memory 709 to control each component of the measurement unit 7, and receives a signal outputted from each component.

The dispensing section 702 is composed of the sample dispenser 74, the reagent dispensers 82 to 84, the R4 reagent dispenser 85, and the R5 reagent dispenser 86. The reagent table section 703 is composed of the reagent tables 75*a* and 75*b*. The reaction section 704 is composed of the primary reaction part 80 and the secondary reaction part 81. The B/F separation section 705 is composed of the primary B/F separator 76*a* and the secondary B/F separator 76*b*. The B/F separation table section 706 is composed of the primary B/F separation table 77*a* and the secondary B/F separation table 77*b*. The mechanism section 707 is composed of the other mechanism parts in the measurement unit 7 and mechanisms in the sample transporting unit 8.

The dispensing section 702 includes a motor 702*m* and a sensor 702*s*. The reagent table section 703 includes a motor 703*m* and a sensor 703*s*. The reaction section 704 includes a motor 704*m* and a sensor 704*s*. The B/F separation section 705 includes a motor 705*m* and a sensor 705*s*. The B/F separation table section 706 includes a motor 706*m* and a sensor 706*s*. The detector 87 includes a motor 87*m* and a sensor 87*s*. The mechanism section 707 includes a motor 707*m* and a sensor 707*s*.

The dispensing section 702, the reagent table section 703, the reaction section 704, the B/F separation section 705, the B/F separation table section 706, the detector 87, and the mechanism section 707 are configured to be driven by the motors 702*m*, 703*m*, 704*m*, 705*m*, 706*m*, 87*m*, and 707*m*, respectively. For example, the sample dispenser 74, the reagent dispensers 82 to 84, the R4 reagent dispenser 85, and the R5 reagent dispenser 86, which constitute the dispensing section 702, each include a pipette (nozzle portion) for aspirating and ejecting the sample, the reagents, and the like, and are each configured to cause the pipette to be moved in the up-down direction or pivoted (turned) by the motor 702m. The reagent tables 75a and 75b, which constitute the reagent table section 703, are each configured to be rotated by the motor 703m.

It is configured that the operation states of the dispensing section 702, the reagent table section 703, the reaction section 704, the B/F separation section 705, the B/F separation table section 706, the detector 87, and the mechanism section 707 are detected by the sensors 702s, 703s, 704s, 705s, 706s, 87s, and 707s, respectively. These sensors include contact-type or transmission-type sensors for detecting the original position (operation start position or operation end position) of each mechanism part, encoders each for detecting the number of pulses of a motor, collision sensors each for detecting collision of a nozzle portion with an obstacle, sensors each for detecting a cuvette held on a table, and the like.

The communication section 708 performs data communication with a communication section 903 of the control apparatus 9. The memory 709 stores a control program to be executed by the controller 701. The memory 709 also stores information of steps and the like regarding each sample in the measurement unit 7 (hereinafter referred to as "individual sample progress information"). A memory 902 stores a suspension time to be used for determining whether the measurement unit 7 discards the sample at an occurrence of an error described below. The individual sample progress information and the suspension time will be described later with reference to FIG. 13 and FIG. 15.

The control apparatus 9 includes a controller 901, the memory 902, the display unit 9a, the input unit 9b, and the communication section 903.

The controller 901 controls each component of the control apparatus 9 by executing a computer program stored in the memory 902, and transmits an operation instruction to the measurement unit 7. The memory 902 is composed of a storage device such as a hard disk, and stores computer programs for causing the control apparatus 9 to operate and for causing the measurement unit 7 to operate.

The display unit 9a is composed of a display and the like, and displays various types of information based on image data. The input unit 9b is composed of a mouse, a keyboard, and the like, and outputs information inputted by the user to the controller 901. The communication section 903 performs data communication with the communication section 708 of the measurement unit 7.

Figure 13:
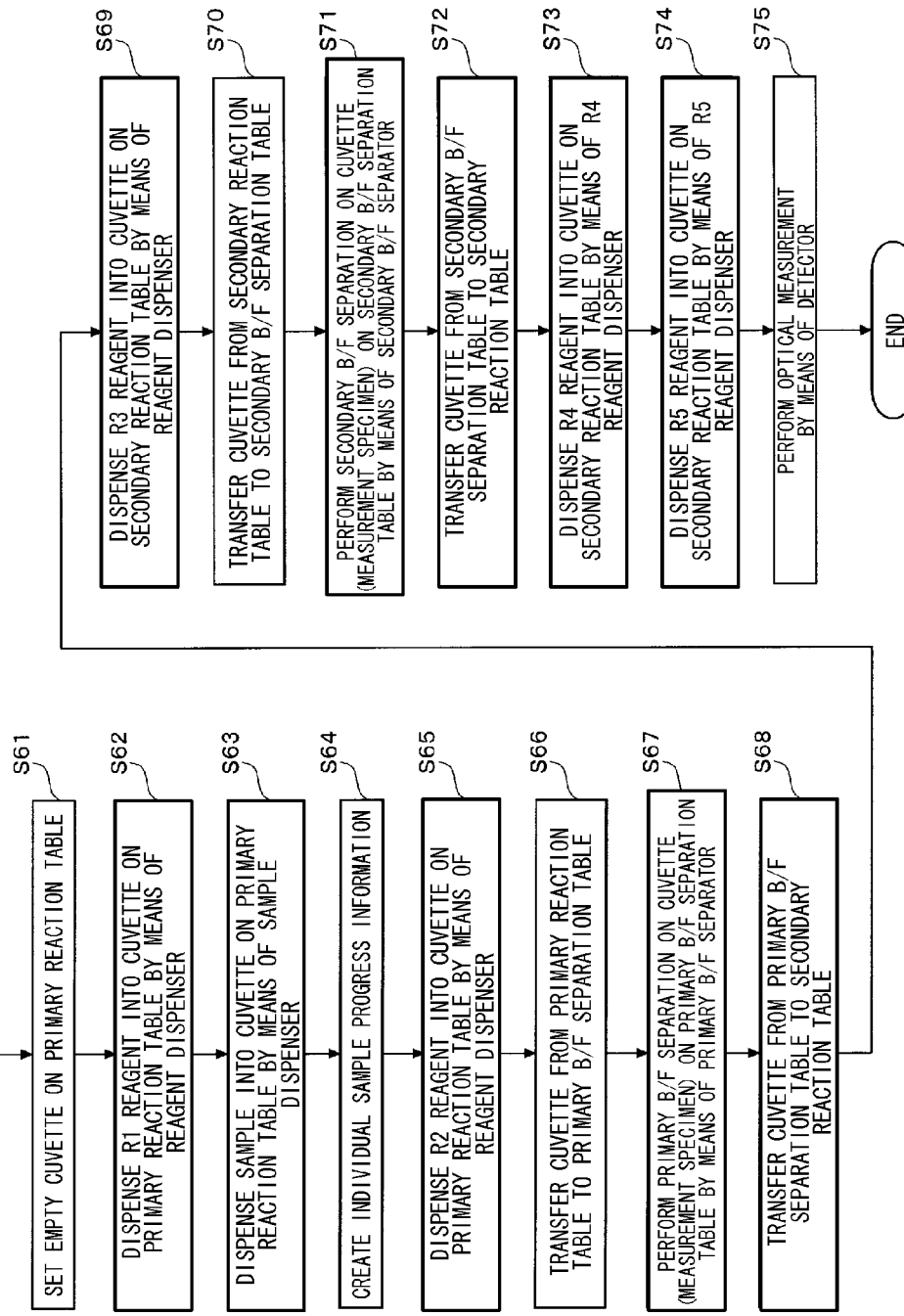
FIG. 13 is a flow chart showing a measurement process performed by the measurement unit according to embodiment 2.

FIG. 13 is a flow chart showing a measurement process performed by the measurement unit 7. The measurement unit 7 of the present embodiment performs in parallel a process composed of a plurality of steps shown in FIG. 13, on a plurality of samples. When the measurement process below is performed, first, a measurement start instruction is inputted by the user via the input unit 9b of the control apparatus 9, and this measurement start instruction is transmitted to the measurement unit 7. Upon receiving the measurement start instruction, the measurement unit 7 drives the sample transporting unit 8 to sequentially transport test tubes 111 to the aspirating position. It should be noted that the processes of S61 to S74 below are performed in parallel on the samples aspirated from test tubes 111.

The controller 701 of the measurement unit 7 drives a cuvette feeder not shown to set an empty cuvette in a holder 80c in the primary reaction table 80a of the primary reaction part 80 (S61).

Next, the controller 701 causes the pipette 82c of the reagent dispenser 82 to aspirate the R1 reagent in a reagent container set on the reagent table 75a. Then, the controller 701 causes the arm 82a to pivot and causes the aspirated R1 reagent to be ejected into the cuvette held in the holder 80c in the primary reaction table 80a (S62)

Next, the controller 701 causes a pipette tip transported by the transporting rack 71a of the urgent sample/tip transporter 71 to be attached to the sample dispenser 74. Then, the controller 701 causes the pipette 74c of the sample dispenser 74 to aspirate a sample such as blood from a test tube 111 placed in a rack 110 transported to the aspirating position by the sample transporting unit 8. Then, the controller 701 causes the arm 74a to pivot and causes the aspirated sample to be ejected into the cuvette in which the R1 reagent has been dispensed (S63).

At this time, with respect to the sample, the controller 701 creates "individual sample progress information" including information of a step being performed in the measurement unit 7 and the like, and stores the "individual sample progress information" in the memory 709 (S64). It should be noted that the individual sample progress information is configured substantially in the same manner as the individual smear preparation information in FIG. 7A described in embodiment 1.

Then, the cuvette containing the R1 reagent and the sample is agitated by the container transporter 80b of the primary reaction part 80, and the R1 reagent and the sample that have been agitated are incubated for a predetermined period of time in the cuvette held in a holder 80c in the primary reaction table 80a.

Next, the controller 701 causes the pipette 83c of the reagent dispenser 83 to aspirate the R2 reagent in a reagent container set on the reagent table 75b. Then, the controller 701 causes the arm 83a to pivot and causes the aspirated R2 reagent to be ejected into the cuvette containing the R1 reagent and the sample that have been incubated for the predetermined period of time (S65).

Then, the cuvette containing the R1 reagent, the sample, and the R2 reagent is agitated by the container transporter 80b of the primary reaction part 80. Then, the R1 reagent, the sample, and the R2 reagent that have been agitated are incubated in the cuvette held in a holder 80c in the primary reaction table 80a for a predetermined period of time. As a result, the capture antibody carried by the magnetic particles contained in the R2 reagent and the antigen contained in the sample are bound to each other.

Next, the controller 701 causes the container transporter 80b of the primary reaction part 80 to transport the cuvette containing the R1 reagent, the sample, and the R2 reagent that have been incubated, to the primary B/F separation table 77a (S66).

Next, the controller 701 causes the magnetic particles in the cuvette held in the primary B/F separation table 77a to be attracted by a magnet located at a lateral side of the cuvette. Then, the controller 701 causes the nozzle portion of the primary B/F separator 76a to be inserted into the cuvette and to aspirate the specimen, thereby removing unreacted components except the magnetic particles and the antigen bound to the magnetic particles via the capture antibody (S67). The cuvette from which the unreacted components have been removed is transferred by rotation of the primary B/F separation table 77a to a position at which the cuvette can be gripped by the arm 78a of the transport mechanism 78.

Next, the controller 701 causes the arm 78a of the transport mechanism 78 to grip the cuvette from which the unreacted components have been removed by the primary B/F separator 76a, and to transport the cuvette to a holder 81c in the secondary reaction table 81a of the secondary reaction part 81 (S68).

Next, the controller 701 causes the pipette 84c of the reagent dispenser 84 to aspirate the R3 reagent in a reagent container set on the reagent table 75a. Then, the controller 701 causes the arm 84a to pivot, and the R3 reagent containing the labeled antibody to be ejected, by a predetermined amount thereof, into the cuvette containing the antigen bound to the magnetic particles via the capture antibody (S69).

Then, the cuvette containing the labeled antibody and the antigen bound to the magnetic particles via the capture antibody is agitated by the container transporter 81b of the secondary reaction part 81. Then, the components in the agitated cuvette are incubated for a predetermined period of time. As a result, the capture antibody, the magnetic particles, the antigen, and the labeled antibody are bound to one another, to form a complex.

Next, the controller 701 causes the container transporter 81b of the secondary reaction part 81 to transport the cuvette containing the incubated components, to the secondary B/F separation table 77b (S70).

Next, the controller 701 causes the magnetic particles in the cuvette held in the secondary B/F separation table 77b to be attracted by a magnet located at a lateral side of the cuvette, as in the step performed by the primary B/F separator 76a. Then, the controller 701 causes the nozzle portion of the secondary B/F separator 76b to be inserted into the cuvette and to aspirate the specimen, thereby removing unreacted labeled antibody that did not form a complex including the magnetic particles (S71). The cuvette from which the unreacted labeled antibody has been removed is transferred by rotation of the secondary B/F separation table 77b, to a position at which the cuvette can be transported by the container transporter 81b of the secondary reaction part 81.

Next, the controller 701 causes the container transporter 81b of the secondary reaction part 81 to transport the cuvette from which the unreacted components have been removed by the secondary B/F separator 76b, to a holder 81c in the secondary reaction table 81a again (S72).

Next, the controller 701 drives the R4 reagent dispenser 85 to eject, from the nozzle portion thereof, the R4 reagent (dispersion liquid) in a reagent container (not shown) that is set below the immune analyzer 6, into the cuvette containing the complex (S73).

Next, the controller 701 drives the R5 reagent dispenser 86 to eject, from the nozzle portion thereof, the R5 reagent in a reagent container (not shown) that is set blow the immune analyzer 6, into the cuvette containing the complex (S74).

Then, the cuvette containing the complex, the dispersion liquid (the R4 reagent) and the R5 reagent containing the luminescent substrate is agitated by the container transporter 81b of the secondary reaction part 81. Then, the components in the agitated cuvette are incubated for a predetermined period of time with the cuvette held in the holder 81c in the secondary reaction table 81a.

Next, the controller 701 causes the transport mechanism part 87a of the detector 87 to transport the cuvette containing the incubated components to a measurement position. Then, the amount of light (amount proportional to the number of photons) generated in the course of the reaction between the labeled antibody in the R3 reagent and the luminescent substrate in the R5 reagent is obtained by means of a photo multiplier tube (not shown) (S75). The obtained measurement result is transmitted to the controller 901 of the control apparatus 9.

Then, the measurement process performed on the sample aspirated from the test tube 111 ends.

Figure 14:
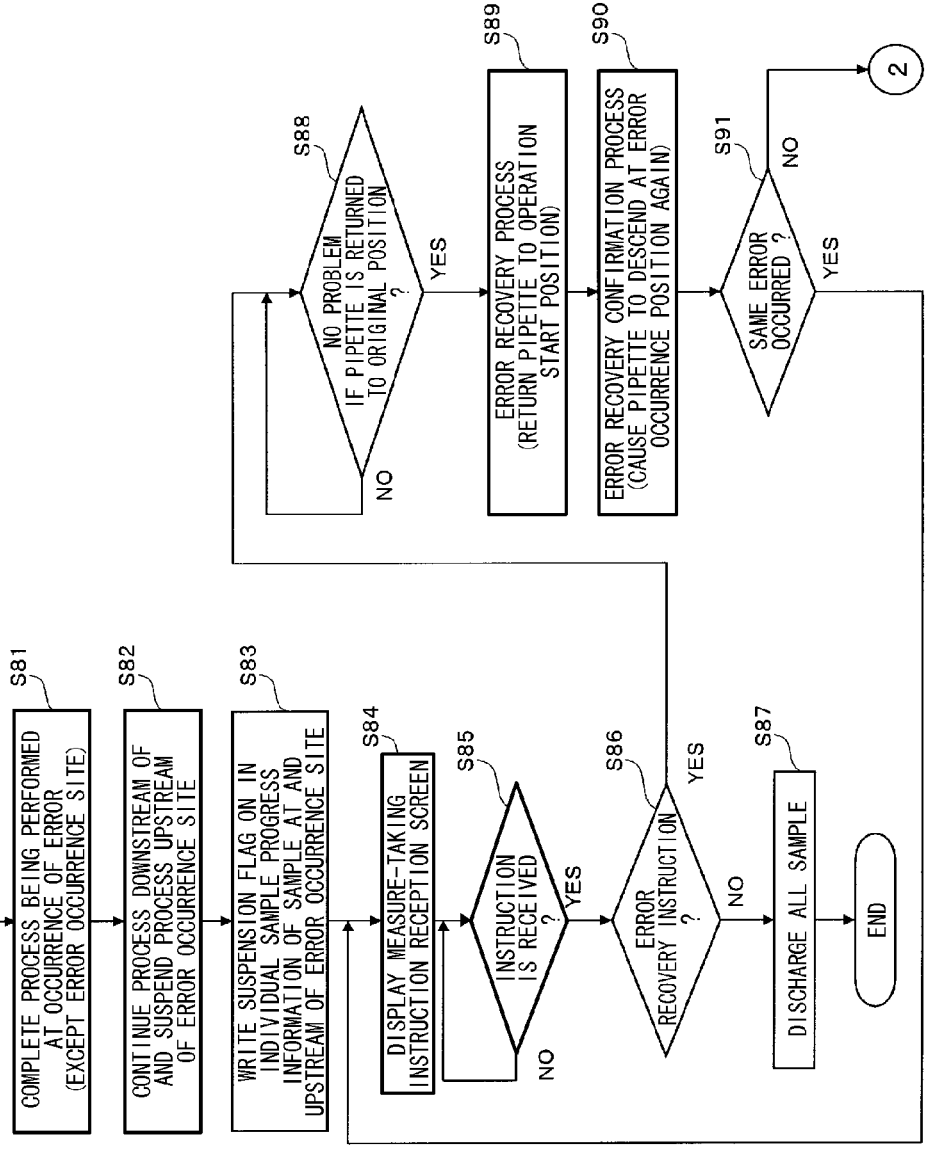
FIG. 14 is a flow chart showing processes performed by the control apparatus in a case where a pipette descending error occurred, according to embodiment 2.

FIG. 14 is a flow chart showing processes performed by the control apparatus 9 in a case where a pipette descending error occurred.

In the present embodiment, as an example of the pipette descending error, an error that may occur when the pipette 83c of the reagent dispenser 83 is caused to descend will be described.

When causing the pipette 83c to descend, the reagent dispenser 83 receives an instruction, from the controller 701 of the measurement unit 7, to rotate the shaft of the motor by the number of drive pulses that corresponds to the distance of the movement of the pipette 83c. However, in a case where the difference between an actual number of pulses of the motor detected by the encoder and the instructed number of drive pulses has a predetermined magnitude or more, it is considered that there may be a temporary failure or the like in a mechanism for causing the pipette 83c to descend. In such a case, the controller 701 transmits to the control apparatus 9 a pipette descending error signal regarding the pipette 83c of the reagent dispenser 83. It should be noted that if the above error has occurred, the controller 701 suspends the process at the error occurrence site.

Upon receiving the pipette descending error signal from the measurement unit 7, the controller 901 of the control apparatus 9 causes processes that were being performed (excluding the process at the error occurrence site) at the time of the occurrence of the error to be completed (S81). Subsequently, the controller 901 causes processes downstream of the error occurrence site to be continued, and processes upstream of the error occurrence site to be suspended (S82). At this time, aspiration of a new sample by the sample dispenser 74 is also suspended.

Here, the processes upstream of the error occurrence site that are caused to be suspended in a case where a pipette descending error occurred in the reagent dispenser 83 are processes of S61 to S66 in FIG. 13. Therefore, the processes to be performed for cuvettes that were held in holders 80c in the primary reaction table 80a at the time of the occurrence of the error, and the processes being performed at the time of the occurrence of the error for causing cuvettes to be held in the primary reaction table 80a, are caused to be suspended. Thus, the sample transporting unit 8, the primary reaction part 80, the reagent dispenser 82, and the sample dispenser 74 stop operating.

The processes downstream of the error occurrence site that are continued to be performed in a case where a pipette descending error occurred in the reagent dispenser 83 are processes for cuvettes that had already left the primary reaction table 80a. Therefore, the processes for the cuvettes held in the primary B/F separation table 77a, the secondary reaction table 81a, and the secondary B/F separation table 77b at the time of the occurrence of the error are continued. Thus, the primary B/F separator 76a, the transport mechanism 78, the secondary reaction part 81, the reagent dispenser 84, the secondary B/F separator 76b, the R4 reagent dispenser 85, the R5 reagent dispenser 86, and the detector 87 continue to operate.

Next, the controller 901 writes "suspension flag ON" in the individual sample progress information of each of the cuvettes for which processes have been suspended (S83). It should be noted that the "suspension flag ON" is written in the same manner as the "suspension flag ON" in the individual smear preparation information in FIG. 7B described in embodiment 1.

Next, the controller 901 causes the display unit 9a to display a measure-taking instruction reception screen (S84). The measure-taking instruction reception screen is configured substantially in the same manner as the measure-taking instruction reception screen 410 in FIG. 10A described in embodiment 1. In the present embodiment, for example, if a pipette descending error has occurred in the reagent dispenser 83, a message, "R2 reagent dispensing step, pipette descending abnormality", and the like are displayed in the message display part 411 shown in FIG. 10A.

With reference back to FIG. 14, when the controller 901 of the control apparatus 9 receives an instruction by the OK button 412 or the forced discharge button 413 being pressed on the measure-taking instruction reception screen (S85: YES), the process is advanced to S86.

When the content of the instruction received in S85 is not an error recovery instruction (S86: NO), that is, when the forced discharge button 413 was pressed, the controller 901 causes all of the samples in the measurement unit 7 to be discharged (S87). Accordingly, the cuvettes containing the samples are emptied, and discarded through the discard hole 88.

On the other hand, when the content of the instruction received in S85 is an error recovery instruction (S86: YES), that is, the OK button 412 was pressed, the controller 901 determines whether there is no problem if the pipette at which the pipette descending error occurred is returned to the operation start position (original position) (S88). That is, at this time, it is determined whether returning the pipette to the operation start position (original position) causes any problem in processes that are being continued on the downstream side of the error occurrence site. For example, in a case where a pipette descending error occurred in the reagent dispenser 83, if the pipette 83c of the reagent dispenser 83 is returned to the operation start position (original position), the arm 83a and the pipette 83c of the reagent dispenser 83 may contact the container transporter 80b transporting, at the time of the occurrence of the error, a cuvette from the primary reaction table 80a to the primary B/F separation table 77a. The controller 901 determines whether such a problem occurs.

Upon determining that there is no problem if the pipette is returned to the operation start position (original position) (S88: YES), the controller 901 performs an error recovery process (S89). Specifically, the controller 901 causes the pipette at which the pipette descending error occurred to be returned to the operation start position (original position). Subsequently, the controller 901 performs an error recovery confirmation process (S90). Specifically, the controller 901 causes the pipette at which the pipette descending error occurred to descend again at the error occurrence position.

In a case where the same error has occurred irrespective of the performance of the error recovery confirmation process (S91: YES), the process is returned to S84. On the other hand, in a case where the same error does not occur as a result of the error recovery confirmation process (S91: NO), the process is advanced to terminal 2.

Figure 15B:
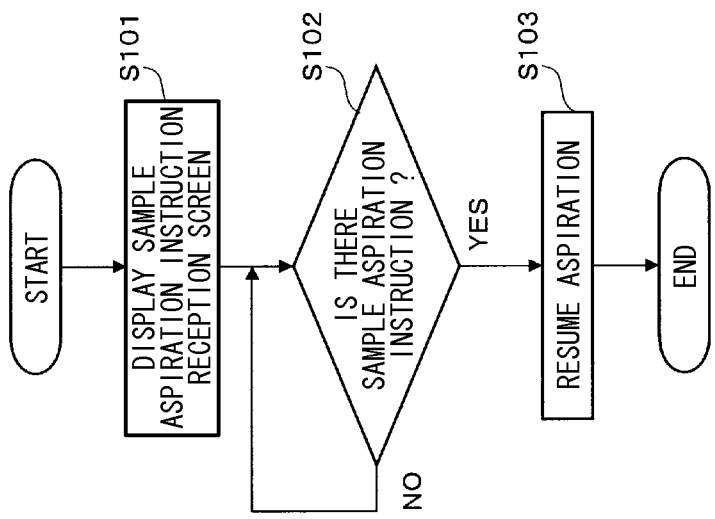
FIG. 15B is a flow chart showing the new sample aspiration resumption process according to embodiment 2.
Figure 15A:
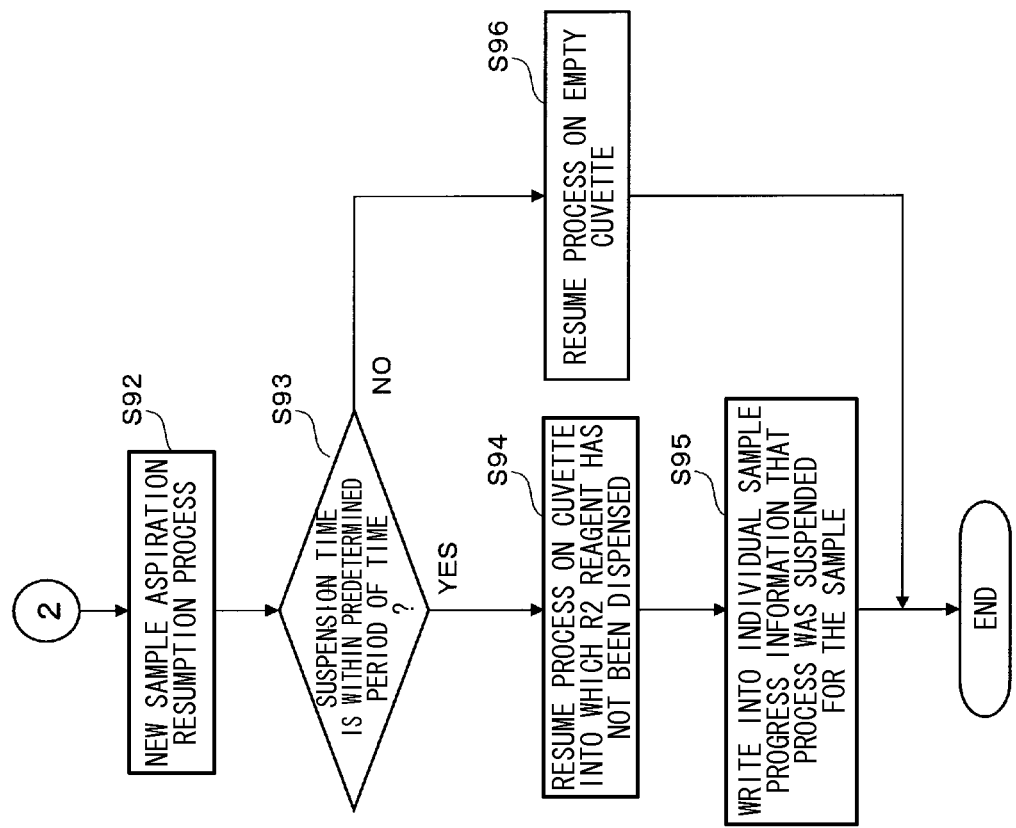
FIG. 15A is a flow chart showing processes performed by the control apparatus in a case where a pipette descending error occurred and a flow chart showing a new sample aspiration resumption process, according to embodiment 2.

FIG. 15A is a flow chart showing processes after the terminal 2 in FIG. 14.

The controller 901 of the control apparatus 9 performs a new sample aspiration resumption process (S92). The new sample aspiration resumption process will be described later with reference to FIG. 15B. Subsequently, the controller 901 reads out the suspension time stored in the memory 902 and determines whether the time period of the suspension is within the read suspension time (S93).

When the time period of the suspension is within the read suspension time (predetermined period of time: 20 minutes, for example) (S93: YES), the controller 901 causes processes to be resumed for cuvettes, among the cuvettes held by the primary reaction table 80a, in which no reagent relating to reaction (the R2 reagent) has been dispensed (S94). Specifically, with respect to the cuvettes held on the primary reaction table 80a, dispensing the sample into cuvettes in which only the R1 reagent has been dispensed, and dispensing the R2 reagent into cuvettes in which the R1 reagent and the sample have been dispensed are resumed. Among the cuvettes for which processes have been suspended, cuvettes in which the R2 reagent has been dispensed are to be discarded. Once the R2 reagent containing the capture antibody is dispensed, the antigen-antibody reaction progresses in the cuvette while the processes are suspended. Therefore, in order to prevent disparity in the reaction time between cuvettes, all of the cuvettes for which the processes have been suspended after the R2 reagent was dispensed are to be discarded. On the other hand, in the cuvettes in which the R2 reagent has not been dispensed (cuvettes in which only the R1 reagent being a buffer has been dispensed, and cuvettes in which the R1 reagent and the sample have been dispensed), the reaction does not progresses. Therefore, unless the liquid in the cuvettes dries due to a long suspension of the processes, resumption of the processes will scarcely affect the analysis results. Therefore, in the present embodiment, in a case where the suspension time is within a predetermined period of time, the cuvettes in which the R1 reagent has been dispensed and the cuvettes in which the R1 reagent and the sample have been dispensed are not to be discarded, and the suspended processes are resumed, thereby keeping the amounts of samples and the R1 reagent that are to be wasted as little as possible. The cuvettes to be discarded are sequentially transported, without reagents being added thereto, to the primary B/F separation table 77a, the secondary reaction table 81a, the secondary B/F separation table 77b, and the detector 87, and emptied at the detector 87, and then discarded through the discard hole 88.

Next, the controller 901 writes, in the individual sample progress information of each of the cuvettes for which the processes were resumed, flag information indicating that suspension of a process occurred for that cuvette (S95). The written flag information is displayed on the display unit 9a along with the measurement result after the measurement on the cuvette ends.

On the other hand, when the time period of the suspension is not within the read suspension time (predetermined period of time) (S93: NO), the controller 901 causes dispensing the R1 reagent into empty cuvettes, among the cuvettes held on the primary reaction table 80a, to be resumed (S96). Cuvettes into which the R1 reagent has been dispensed and cuvettes into which the R1 reagent and the sample have been dispensed are all to be discarded. The reason why the cuvettes into which the R2 reagent has been dispensed are to be discarded is the same as that described before. The reason why the cuvettes into which the R1 reagent has been dispensed are to be discarded is that the liquid in the cuvettes may dry due to the long suspension of the processes. The cuvettes to be discarded are sequentially transported, without reagents being dispensed therein, to the primary B/F separation table 77a, the secondary reaction table 81a, the secondary B/F separation table 77b, and the detector 87, and emptied at the detector 87, and then discarded through the discard hole 88.

FIG. 15B is a flow chart showing the new sample aspiration resumption process performed in S92.

The controller 901 of the control apparatus 9 causes the display unit 9a to display a sample aspiration instruction reception screen (S101). The sample aspiration instruction reception screen of the present embodiment is the same as the sample aspiration instruction reception screen 420 in FIG. 10B described in embodiment 1. Upon determining that the OK button 421 of the sample aspiration instruction reception screen 420 has been pressed (S102: YES), the controller 901 transmits an aspiration instruction signal to the measurement unit 7, and causes the sample dispenser 74 of the measurement unit 7 to resume aspiration of a new sample (S103). Then, the new sample aspiration resumption process ends.

In the present embodiment, description has been given of an exemplary case where a pipette descending error has occurred in the reagent dispenser 83 (the process of step S65 has been suspended). However, the present invention can be applied to any case in which a pipette descending error has occurred in the sample dispenser 74, the reagent dispenser 82, or the reagent dispenser 84.

As described above, according to the present embodiment, in a case where a pipette descending error has occurred, processes upstream of the error occurrence site are suspended, and then an error recovery process for returning the pipette to the operation start position (original position) is performed. Accordingly, relatively minor errors such as a temporary failure of a mechanism for causing a pipette to descend can be solved.

Moreover, in this case, processes downstream of the error occurrence site are continued. Accordingly, processes of the samples that have passed the error occurrence site can be promptly completed.

Moreover, according to the present embodiment, in a case where the suspension time is within a predetermined period of time when the error is solved, the upstream processes that were suspended are resumed. This eliminates the necessity to discard all of the samples for which processes were suspended, which eliminates the necessity to use the reagents and the like again for the samples. Accordingly, the amount of consumables to be discarded can be reduced. Reduction of the amount of consumables to be discarded is also effective for environmental conservation.

Further, in this case, in the individual sample progress information of each sample for which a process was suspended, flag information indicating that the process was suspended is written. Moreover, the individual sample progress information of each sample for which the process was suspended is displayed on the display unit 9a. Accordingly, the user can distinguish samples for which processes ended without having been suspended, and samples for which the processes were suspended.

Further, according to the present embodiment, unless the suspension time is within a predetermined period of time when the error is solved, samples to which reagents relating to reactions have been dispensed, among samples upstream of the error occurrence site, are to be discarded. However, processes for empty cuvettes held on the primary reaction table 80a are resumed. Accordingly, processes of samples can be promptly resumed.

Although the embodiments of the present invention have been described as above, embodiments of the present invention are not limited thereto.

For example, in the above embodiments, blood is used as the sample to be measured. However, urine can also be measured. That is, the present invention can be applied to a sample processing system for testing urine. Further, the present invention can be applied to a laboratory sample processing system for testing other laboratory samples.

Further, in the above embodiments, the error recovery confirmation process is performed after the error recovery process is performed. However, the embodiments of the present invention are not limited thereto, and the error recovery process may be omitted.

Further, in embodiment 1, after all of the blood samples that have been aspirated at the time of occurrence of the error arrive at the staining part 50 (after the processes of S14 to S17 in FIG. 6) and a sample aspiration instruction is issued, aspiration of a new sample is resumed. However, the embodiment is not limited thereto. After predetermined processes that are to be performed on all of the samples (for example, processes of S14 to S15 in FIG. 6) have ended, aspiration of a new sample may be resumed.

Further, in embodiment 2, aspiration of a new sample is resumed after a sample aspiration instruction is issued. However, the embodiment is not limited thereto. After predetermined processes that are to be performed to all of the samples (for example, processes of S61 to S69 in FIG. 13) have ended, aspiration of a new sample may be resumed.

Further, in the above embodiments, in the new sample aspiration resumption process, aspiration of a new sample is resumed after a sample aspiration instruction is issued. However, the embodiments are not limited thereto. At the time when the upstream processes that have been suspended are resumed, aspiration of a new sample may be automatically resumed.

In the above embodiments, the error recovery process is performed when the OK button 412 is pressed by the user on the measure-taking instruction reception screen 410 in FIG. 10. However, the embodiments are not limited thereto. The error recovery process may be automatically performed by the controller 201 of the smear preparing apparatus 2 or the controller 901 of the control apparatus 9. Further, in such an embodiment where the error recovery process is automatically performed, the error recovery process may be automatically performed for a predetermined number of times (for example, 3 times), and in a case where the error is not solved irrespective of the performance of the automatic error recovery process, the user may be notified of the error.

In the above embodiments, in a case where the error is not solved irrespective of the performance of the error recovery process, the measure-taking instruction reception screen 410 in FIG. 10 is displayed again to receive an error recovery instruction. However, the error recovery process may be repeatedly performed, once an error recovery instruction is received, until the error is solved. In this case, in a case where the error is still not solved after the error recovery process is repeated for a predetermined period of time (or predetermined number of times), an instruction from the user may be received again.

In the above embodiments, upon detection of an error, processes are suspended and wait until an instruction from the user is received, and the error recovery process is unconditionally performed upon reception of an error recovery instruction. However, the embodiments are not limited thereto. Specifically, in embodiment 1, in a case where a predetermined period of time has elapsed after an error is detected, cassettes for which processes have been suspended may automatically be discharged without waiting for an error recovery instruction. In embodiment 2, in a case where a predetermined period of time has elapsed after an error is detected, cuvettes in which at least one of the R1 reagent, the R2 reagent, and the sample has been dispensed, among cuvettes held on the primary reaction table 80a, may be discharged without waiting for an error recovery instruction.

In the above embodiments, in a case where a predetermined error described above has occurred, processes of samples downstream of the error occurrence site are continued. However, the embodiments are not limited thereto. If an error has occurred, processes of samples downstream of the error occurrence site are suspended, and then, at a predetermined timing (for example, after the error recovery confirmation process is performed), the processes of the downstream samples may be resumed.

In embodiment 1, in a case where a cassette arrival error or a cassette send-out error has occurred, the process to take measures against the error is performed by the smear preparing apparatus 2. However, the embodiment is not limited thereto. The process to take measures against the error may be performed by another control apparatus.

In embodiment 2, in a case where a pipette descending error has occurred, a process to take measures against the error is performed by the control apparatus 9. However, the embodiment is not limited thereto. The process to take measures against the error may be performed by the measurement unit 7.

In embodiment 2, unless the suspension time is within a predetermined period of time, all of the samples that are located upstream of the error occurrence site and in which the R1 reagent has been dispensed, and all of the samples that are located upstream of the error occurrence site and in which the R2 reagent has been dispensed are discarded. However, all of the samples in which the R2 reagent has been dispensed and a part of the samples in which the R1 reagent has been dispensed may be discarded. In this case, for example, if the suspension time is about the same as the predetermined period of time, processes of samples whose analysis results will probably be obtained without problem are resumed. Accordingly, processes that are performed to no avail for samples whose appropriate process results will hardly be obtained due to a long process suspension time can be omitted, and at the same time, samples whose appropriate process results will probably be obtained due to a short process suspension time will not be wasted.

In addition to the above, various modification of the embodiment of the present invention may be made without departing from the scope of the technical idea defined by the claims.

What is claimed is:

1. A sample processing apparatus which processes a plurality of samples, the sample processing apparatus comprising:
   a plurality of components, each performing a respective operation on a respective sample in a sequential processing;
   a transfer section which transfers the plurality of samples to the plurality of components according to a flow in said sequential processing;
   a sensor configured to detect an error indicating that an operation of a portion of the transfer section was not performed successfully;
   a display; and
   a controller programmed to:
   in response to the sensor detecting the error, control the plurality of components to interrupt the sequential processing for a first sample that has not reached the portion of the transfer section at which the error was detected by the sensor while continuing the sequential processing for a second sample that passed the portion of the transfer section at which the error was detected by the sensor, and control the display to display a first instruction part for receiving a first instruction and a second instruction part for receiving a second instruction,
   in response to the first instruction selected by a user, control the transfer section to retry the operation of the portion of the transfer section for the first sample, and control the plurality of components to resume the interrupted process of the first sample when the retried operation for the first sample has been performed successfully, and
   in response to the second instruction selected by the user, control the transfer section to discharge the first sample, wherein the controller is further programmed to add a first indicator into individual smear preparation information for each of the first sample which is different from a second indicator in the individual smear preparation information for each of the second sample and further programmed to add to the individual smear preparation information for said each of the first sample an indicator indicating a position Where the respective first sample was located at the time of the error.

2. The sample processing apparatus according to claim 1, wherein
   the controller is programmed to control the components and the transfer section to complete operations being performed on the second sample before the controller is programmed to control the components and the transfer section to interrupt the sequential processing of the plurality of samples.

3. The sample processing apparatus according to claim 1, further comprises an aspirator for aspirating a sample from a sample container as one of the components, wherein:
   the controller is programmed to control the aspirator to interrupt an aspiration of a new sample from a sample container in response to the sensor detecting the error, and to resume the aspiration in response to the retry operation being performed successfully.

4. The sample processing apparatus according to claim 3, further comprising a rack transporter which transports a sample rack holding a plurality of sample containers, wherein
   upon receiving an instruction to start the process for a plurality of samples, the controller is programmed to control the aspirator to sequentially aspirate the plurality of samples from the plurality of sample containers held by the sample rack.

5. The sample processing apparatus according to claim 3, wherein:
   in response to the sensor detecting the error, the controller is programmed to control the aspirator to interrupt an aspiration on an aspirated sample that has not reached the portion of the transfer section at which the operation was not performed successfully, and
   in response to the retry operation being performed successfully, the controller is programmed to control the aspirator to resume the interrupted process for the aspirated sample.

6. The sample processing apparatus according to claim 5, wherein:
   in response to the sensor detecting the error, the controller is programmed to control the aspirator to interrupt dispensing a reagent into a cuvette as the operation for the aspirated sample, and
   in response to the retry operation being performed successfully, the controller is programmed to control the aspirator to resume dispensing the reagent.

7. The sample processing apparatus according to claim 5, wherein
   in response to the retry operation being performed successfully, the controller is programmed to determine whether resuming the interrupted operation is possible based on a time elapsed from the interruption, and
   in response to the controller determining that the resuming is possible, the controller is programmed to control the aspirator to resume the interrupted operation.

8. The sample processing apparatus according to claim 5, wherein in response to interrupting operations of said sequential processing on at least two of the plurality of samples, the controller is programmed to determine, for each of the at least two interrupted samples whether resuming said sequential processing is possible based on a time elapsed from the interruption.

9. The sample processing apparatus according to claim 1, further comprising an output section which outputs a result of the process, wherein:
the controller is programmed to control the output section to output a result of the sequential processing comprising said interruption and the resumption such that the result is output differently from a result output from an uninterrupted process, and
wherein the output result comprises at least an identification of a respective sample of the plurality of samples and a preparation result that indicates whether the error occurred during the sequential processing.

10. The sample processing apparatus according to claim 1, wherein
the controller is programmed to determine that the operation was not performed successfully in response to the first sample not being carried into a component by the transfer section as required by the sequential processing or in response to the first sample not being carried out of the component by the transfer section as required by the sequential processing.

11. The sample processing apparatus according to claim 10, wherein
in response to the sensor detecting that the respective sample is not transferred by the transferring section from a first component to a second component as required by said sequential processing, the controller is further programmed to control the transfer section to transfer the respective sample in a direction opposite to a direction from the first component to the second component and then to retry transfer the respective sample from the first component to the second component again.

12. The sample processing apparatus according to claim 11, wherein:
the controller is programmed to control the transfer section to transfer the first sample in the opposite direction at a timing at which no operation that interferes with the opposite direction transfer is performed by any of the plurality of components.

13. The sample processing apparatus according to claim 1, wherein
in response to an operation of a component from the plurality of components being not performed successfully, the controller is further programmed to control the component to recover to a state where the component restarts the operation, and further programmed to control the component to retry the operation.

14. The sample processing apparatus according to claim 1, further comprising a display, wherein
in response to the sensor detecting the error, the controller is further programmed to control the display to display the error.

15. The sample processing apparatus according to claim 14, wherein
the controller is programmed to receive an instruction whether to cause the retry operation, and in response to receiving the instruction, the controller is programmed to control at least one of the component and the transfer section to retry the operation.

16. The sample processing apparatus according to claim 1, wherein the controller is further programmed to control the transfer section which is a belt to move backwards during the retrying and to attempt to return the first sample to a predetermined stopping position for the sequential processing during the resume operation.

17. A sample processing method for processing a plurality of sample, the method comprising:
transferring the plurality of samples to a plurality of components, according to a flow in a sequential processing, each of the components performing a respective operation on a respective sample in the sequential processing;
detecting an error indicating that an operation of the transferring was not performed successfully;
in response to the detecting the error, interrupting the sequential processing for a first sample that has not reached an operation in which the error is detected, while continuing the sequential processing for a second sample that completed the operation in which the error is detected;
displaying instruction part configured to receive a first instruction and a second instruction part configured to receive a second instruction;
in response to the first instruction part receiving the first instruction selected by a user, retrying the operation in which the error is detected for the first sample and resuming the interrupted sequential processing for the first sample in response to the retrying the operation for the first sample being performed successfully, and
in response to the second instruction part receiving a second instruction selected by the user, discharging the first sample,
wherein the method further comprises: adding a first indicator into individual smear preparation information for each of the first sample which is different from a second indicator in the individual smear preparation information for each of the second sample, and adding to the individual smear preparation information for said each of the first sample an indicator indicating a position where the respective first sample was located at the time of the error.

18. The method according to claim 17, wherein
in response to the detecting the error, the interrupting causes an uncompleted operation in the sequential flow on the first sample to be completed, and then interrupts a next operation in the sequential flow to be performed to the first sample.

19. The method according to claim 17, wherein
in response to the detecting the error step, interrupting an aspiration of a new sample from a sample container, and in response to the retrying operation step being performed successfully, the resuming causes the aspiration of the new sample from the sample container to be resumed.

20. A sample processing apparatus which sequentially processes a plurality of samples, the sample processing apparatus comprising:
a plurality of components, each performing a respective operation on a respective sample in the sequential processing;
a transfer section which transfers the plurality of samples to the components according to a flow in said sequential processing;
a sensor configured to detect an error indicating that the operation of a portion of the transfer section was not performed successfully;
a display; and
a controller which is programmed to:

in response to the sensor detecting the error, control the transfer section to continue the sequential processing for a second sample that has passed the portion of the transfer section in which the sensor detected the error and control the display to display a user interface which is configured to receive user input comprising one of a first instruction and a second instruction;

in response to the user interface receiving the first instruction as the user input, executing a retry operation comprising moving the portion of the transfer section where the error was detected by a predetermined distance to resume processing of a first sample, and in response to the user interface receiving the second instruction as the user input, control the transfer section to discharge the first sample, and to add a first indicator into individual smear preparation information for each of the first sample which is different from a second indicator in the individual smear preparation information for each of the second sample and to add to the individual smear preparation information for said each of the first sample an indicator indicating a position where the respective first sample was located at the time of the error.

21. The sample processing apparatus according to claim 20, wherein in response to the retry operation being successfully performed, the controller is further programmed to determine whether the interrupted operation can be resumed based on a time elapsed from the interruption, and in response to the controller determining that the interrupted operation can be resumed, the controller is further programmed to resume the interrupted operation.

22. The sample processing apparatus according to claim 20, wherein the plurality of components comprise a reagent dispenser which is configured to dispense a reagent into a cuvette in which the respective sample has been dispensed, and the controller is programmed to control the plurality of components to discard the cuvette in which the reagent has been dispensed by the regent dispenser, wherein the cuvette had not reached at least one of the component and the portion of the transfer section where the error is detected by the sensor.

* * * * *